(12) United States Patent
Narimatsu

(10) Patent No.: US 6,251,081 B1
(45) Date of Patent: Jun. 26, 2001

(54) BLOOD-PRESSURE MONITORING APPARATUS

(75) Inventor: Kiyoyuki Narimatsu, Kasugai (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/392,236

(22) Filed: Sep. 8, 1999

(30) Foreign Application Priority Data

Oct. 1, 1998 (JP) .................................................. 10-279680

(51) Int. Cl.$^7$ ...................................................... A61B 5/02
(52) U.S. Cl. ........................................... 600/490; 600/485
(58) Field of Search .................................... 600/300–301, 600/500–508, 481–491; 128/897–899, 920–925

(56) References Cited

U.S. PATENT DOCUMENTS 5,131,391 7/1992 Sakai et al. .
5,906,581 * 5/1999 Tsuda ................................... 600/485
6,036,651 * 3/2000 Inukai et al. ........................ 600/485
6,045,510 * 4/2000 Ogura et al. ........................ 600/485

FOREIGN PATENT DOCUMENTS

| 0 619 093 A1 | 10/1994 | (EP) . |
| 2 281 780 | 3/1995 | (GB) . |
| 4-261640 | 9/1992 | (JP) . |

* cited by examiner

Primary Examiner—Angela D. Sykes
Assistant Examiner—Ryan Carter
(74) Attorney, Agent, or Firm—Oliff & Berridge PLC

(57) ABSTRACT

A blood-pressure monitoring apparatus including a measuring device which periodically measures a blood-pressure value of a living subject at a predetermined period, and a predicting device or circuit which predicts, based on the blood-pressure values measured by the measuring device, a blood-pressure value of the living subject at a time later by a predetermined time than a time when the last one of the blood-pressure values is measured by the measuring device.

20 Claims, 9 Drawing Sheets

PREDICTED BLOOD PRESSURE PBP

BLOOD-PRESSURE MONITORING APPARATUS

BACKGROUND OF THE INVENTION

1. Field of the Invention

The present invention relates to a blood-pressure monitoring apparatus which monitors the blood pressure of a living subject by periodically measuring a blood-pressure value of the subject.

2. Related Art Statement

There is known a blood-pressure ("BP") monitoring device which monitors the BP of a living subject, e.g., a patient, by periodically measuring a BP value of the subject. An example of the conventional BP monitoring device is disclosed in Japanese Patent Application laid open for public inspection under Publication No. 4(1992)-261640. The BP monitoring device includes a display device which displays each of the periodically measured BP values when each BP value is measured, or a graph representing a time-wise trend or change of the periodically measured BP values.

Even a patient whose BP needs to be monitored has a constant tendency or rate of change of his or her BP, in a short period of time. That is, in a short period, a patient's BP does not change irregularly. Hence, a BP monitoring device which displays a graph representing a time-wise trend of BP values periodically measured from a patient is employed by a doctor for predicting a future BP value of the patient. Even though the last or current BP value measured from the patient may not be abnormal, if the doctor can predict from the time-wise trend of the measured BP values that the patient's BP will be abnormal in future, the doctor can immediately give necessary treatments for the patient.

However, a doctor may not be able to check each of the BP values periodically measured from of a patient. Hence, there has been proposed a BP monitoring device of a type which generates an alarm sound, when judging that a measured BP value does not fall within a predetermined normal BP range, so that the doctor may be informed of the occurrence of an abnormality to the patient. However, so long as each measured BP value falls within the normal BP range, the conventional BP monitoring device does not take any actions, even in the case where a doctor would be able to predict that the patient's BP will be abnormal in future. Therefore, there are some cases where a long time passes before the BP monitoring device generates an alarm sound, after the patient's BP indicates its abnormality. Even in the case where the doctor can check each of the periodically measured BP values of the patient, the doctor may not be able to make an appropriate judgment.

SUMMARY OF THE INVENTION

It is therefore an object of the present invention to provide a blood-pressure monitoring apparatus which predicts a future blood-pressure value of a living subject or a future change of the blood pressure of the living subject.

The present invention provides a blood-pressure monitoring apparatus which has one or more of the technical features that are described below in respective paragraphs given parenthesized sequential numbers (1) to (20). Any technical feature which includes another technical feature shall do so by referring, at the beginning, to the parenthesized sequential number given to that technical feature.

(1) According to a first feature of the present invention, there is provided a blood-pressure monitoring apparatus comprising a measuring device which periodically measures a blood-pressure value of a living subject at a predetermined period; and predicting means for predicting, based on a plurality of blood-pressure values measured by the measuring device, a blood-pressure value of the living subject at a later time later by a predetermined time than a time when a last one of the plurality of blood-pressure values is measured by the measuring device. The predicting means predicts, based on the blood-pressure ("BP") values measured by the measuring device, a BP value of the living subject at the later time, i.e., determines a predicted BP value of the subject that is predicted to be most probably measured by the measuring device at the later time. Therefore, the living subject such as a patient, or a medical person such as a doctor or a nurse who attends to the patient can more quickly take appropriate actions, or give appropriate treatments to the patient, in view of the predicted BP value.

(2) According to a second feature of the present invention that includes the first feature (1), the predicting means comprises a central-value determining means for determining, as the predicted blood-pressure value, a central value of a blood-pressure range within which the blood pressure of the living subject is predicted, based on the plurality of blood-pressure values, to fall at the later time. The central-value determining means may determine the central value of the blood-pressure range within which the BP of the subject is predicted to fall at the later time, by applying the method of least squares, for example, to the BP values measured by the measuring device.

(3) According to a third feature of the present invention that includes the first or second feature (1) or (2), the measuring device comprises an inflatable cuff, the measuring device periodically measuring a blood-pressure value of the living subject while changing a pressing pressure of the cuff applied to a body portion of the subject. In this case, the measuring device non-invasively measures a BP value of the subject, which leads to relieving the subject of the burden of being physically invaded for a BP measurement using, e.g., a catheter.

(4) According to a fourth feature of the present invention that includes any one of the first to third features (1) to (3), the monitoring apparatus further comprises period changing means for changing, when the predicted blood-pressure value does not fall within a reference blood-pressure range, the predetermined period to a changed period shorter than the predetermined period, so that the measuring device measures a blood-pressure value of the living subject at the changed period. The fact that the predicted BP value does not fall within the reference BP range means that the BP of the subject will go out of the reference BP range in future. In this case, the period changing means changes the predetermined period to a changed period shorter than the predetermined period. Therefore, the measuring device will measure a BP value of the subject at the shorter period, i.e., earlier or more frequently. If the thus measured BP value does not fall within the reference BP range, the present BP monitoring apparatus may generate an alarm sound to inform the subject, or the medical person, of the occurrence of abnormality. However, the reference BP range may be replaced with a single reference BP value, according to the fifth or sixth feature (5) or (6) described below.

(5) According to a fifth feature of the present invention that includes any one of the first to third features (1) to (3), the monitoring apparatus further comprises period changing means for changing, when the predicted blood-pressure value is greater than a reference blood-pressure value, the predetermined period to a changed period shorter than the predetermined period, so that the measuring device measures a blood-pressure value of the living subject at the changed period.

(6) According to a sixth feature of the present invention that includes any one of the first to third features (1) to (3), the monitoring apparatus further comprises period changing means for changing, when the predicted blood-pressure value is smaller than a reference blood-pressure value, the predetermined period to a changed period shorter than the predetermined period, so that the measuring device measures a blood-pressure value of the living subject at the changed period.

(7) According to a seventh feature of the present invention that includes any one of the first to sixth features (1) to (6), the monitoring apparatus further comprises measured-blood-pressure-value displaying means for displaying a graph representing a time-wise trend of the plurality of blood-pressure values measured by the measuring device, on a two-dimensional coordinate system defined by a first axis indicative of a plurality of times at which the plurality of blood-pressure values are measured by the measuring device, respectively, and a second axis indicative of the plurality of blood-pressure values measured by the measuring device; and predicted-blood-pressure-value displaying means for displaying, on the coordinate system, a graph representing the blood-pressure value predicted by the predicting means. In this case, the graph representing the BP value predicted by the predicting means is displayed on the two-dimensional coordinate system on which the graph representing the time-wise trend of the BP values measured by the measuring device is displayed. Thus, the subject or the medical person can easily and objectively see the future change of BP of the subject, on the coordinate system.

(8) According to an eighth feature of the present invention that includes any one of the first to sixth features (1) to (6), the monitoring apparatus further comprises a probability calculating means for calculating a probability with which a blood-pressure value of the living subject measured by the measuring device at the later time is equal to the predicted blood-pressure value, according to a predetermined relationship between time and probability; probability-distribution a calculating means for calculating, based on the calculated probability, a normal distribution of probability of the blood-pressure value of the living subject measured by the measuring device at the later time; and range determining means for determining a blood-pressure range whose central value is equal to the predicted blood-pressure value and within which the blood-pressure value of the living subject measured by the measuring device at the later time falls within a predetermined probability. In this case, the range determining means determines the BP range within which the BP value of the subject measured by the measuring device at the later time falls with the predetermined probability. Therefore, the medical person can make an accurate judgment about whether or not he or she should give a quick treatment to his or her patient.

(9) According to a ninth feature of the present invention that includes the eighth feature (8), the monitoring apparatus further comprises period changing means for changing, when at least one of an upper limit value and a lower limit value of the determined blood-pressure range does not fall within a reference blood-pressure range, the predetermined period to a changed period shorter than the predetermined period, so that the measuring device measures a blood-pressure value of the living subject at the changed period. The fact that the upper and/or lower limit value of the BP range determined by the range determining means does not fall within the reference BP range means that the BP of the subject will go out of the reference BP range in future. In this case, the period changing means changes the predetermined period to a changed period shorter than the predetermined period. Therefore, the measuring device will measure a BP value of the subject at the shorter period, i.e., earlier or more frequently. If the thus measured BP value does not fall within the reference BP range, the present BP monitoring apparatus may generate an alarm sound to inform the subject, or the medical person, of the occurrence of abnormality. However, the reference BP range may be replaced with a reference BP value, according to the tenth or eleventh feature (10) or (11) described below.

(10) According to a tenth feature of the present invention that includes the eighth feature (8), the monitoring apparatus further comprises period changing means for changing, when at least one of an upper limit value and a lower limit value of the determined blood-pressure range is greater than a reference blood-pressure value, the predetermined period to a changed period shorter than the predetermined period, so that the measuring device measures a blood-pressure value of the living subject at the changed period.

(11) According to an eleventh feature of the present invention that includes the eighth feature (8), the monitoring apparatus further comprises period changing means for changing, when at least one of an upper limit value and a lower limit value of the determined blood-pressure range is smaller than a reference blood-pressure value, the predetermined period to a changed period shorter than the predetermined period, so that the measuring device measures a blood-pressure value of the living subject at the changed period.

(12) According to a twelfth feature of the present invention that includes any one of the eighth to eleventh features (8) to (11), the monitoring apparatus further comprises measured-blood-pressure-value displaying means for displaying a graph representing a time-wise trend of the plurality of blood-pressure values measured by the measuring device, on a two-dimensional coordinate system defined by a first axis indicative of a plurality of times at which the plurality of blood-pressure values are measured by the measuring device, respectively, and a second axis indicative of the plurality of blood-pressure values measured by the measuring device; predicted-blood-pressure-value displaying means for displaying, on the coordinate system, a graph representing the blood-pressure value predicted by the predicting means; and range displaying means for displaying, on the coordinate system, a graph representing the blood-pressure range determined by the range determining means. In this case, the graph representing the BP value predicted by the predicting means and the graph representing the blood-pressure range determined by the range determining means are displayed on the two-dimensional coordinate system on which the graph representing the time-wise trend of the BP values measured by the measuring device is displayed. Thus, the subject or the medical person can easily and objectively know the range and probability of change of the BP of the subject, on the coordinate system.

(13) According to a thirteenth feature of the present invention that includes any one of the first to twelfth features (1) to (12), the monitoring apparatus further comprises pulse-wave-propagation-information obtaining means for iteratively obtaining, from the living subject, a set of information relating to propagation of a pulse wave through an arterial vessel of the subject; estimating means for iteratively estimating a blood-pressure value of the living subject, based on each set of information of the iteratively obtained sets of information, according to a predetermined relationship between pulse-wave-propagation information and blood pressure; and predicted-blood-pressure-value modifying means for modifying, based on the estimated blood-pressure value, the blood-pressure value predicted by the predicting means. In this case, the predicted-BP-value modifying means modifies, based on the estimated BP value or values, the BP value predicted by the predicting means. Thus, the present BP monitoring apparatus provides a more accurate predicted BP value of the subject.

(14) According to a fourteenth feature of the present invention that includes the thirteenth feature (13), the monitoring apparatus further comprises period changing means for changing, when the predicted blood-pressure value does not fall within a reference blood-pressure range, the predetermined period to a changed period shorter than the predetermined period, so that the measuring device measures a blood-pressure value of the living subject at the changed period; and period re-changing means for re-changing, when the modified blood-pressure value falls within the reference blood-pressure range after the predetermined period is changed to the changed period, the changed period back to the predetermined period, so that the measuring device measures a blood-pressure value of the living subject at the predetermined period. The fact that the modified BP value falls within the reference BP range after the predetermined period is changed to the changed period means that the BP of the subject that has been predicted to go out of the reference BP range is now predicted not to go out of the reference BP range. Accordingly, the period re-changing means re-changes the changed period back to the initial, predetermined period. Thus, the measuring device measures a BP value of the subject at the predetermined period, which leads to relieving the subject of the burden of being measured at the short period. However, the reference BP range may be replaced with a single reference BP value, according to the fifteenth or sixteenth feature (15) or (16) described below.

(15) According to a fifteenth feature of the present invention that includes the thirteenth feature (13), the monitoring apparatus further comprises period changing means for changing, when the predicted blood-pressure value is greater than a reference blood-pressure value, the predetermined period to a changed period shorter than the predetermined period, so that the measuring device measures a blood-pressure value of the living subject at the changed period; and period re-changing means for re-changing, when the modified blood-pressure value is not greater the reference blood-pressure value after the predetermined period is changed to the changed period, the changed period back to the predetermined period, so that the measuring device measures a blood-pressure value of the living subject at the predetermined period.

(16) According to a sixteenth feature of the present invention that includes the thirteenth feature (13), the monitoring apparatus further comprises period changing means for changing, when the predicted blood-pressure value is smaller than a reference blood-pressure value, the predetermined period to a changed period shorter than the predetermined period, so that the measuring device measures a blood-pressure value of the living subject at the changed period; and period re-changing means for re-changing, when the modified blood-pressure value is not smaller than the reference blood-pressure value after the predetermined period is changed to the changed period, the changed period back to the predetermined period, so that the measuring device measures a blood-pressure value of the living subject at the predetermined period.

(17) According to a seventeenth feature of the present invention that includes any one of the thirteenth to sixteenth features (13) to (16), the monitoring apparatus further comprises probability calculating means for calculating a probability with which a blood-pressure value of the living subject measured by the measuring device at the later time is equal to the predicted blood-pressure value, according to a predetermined relationship between time and probability; probability-distribution calculating means for calculating, based on the calculated probability, a normal distribution of probability of the blood-pressure value of the living subject measured by the measuring device at the later time; and range determining means for determining a blood-pressure range whose central value is equal to the predicted blood-pressure value and within which the blood-pressure value of the living subject measured by the measuring device at the later time falls with a predetermined probability.

(18) According to an eighteenth feature of the present invention that includes the seventeenth feature (17), the probability calculating means comprises means for calculating a probability with which a blood-pressure value of the living subject measured by the measuring device at the later time is equal to the modified blood-pressure value, according to the predetermined relationship between time and probability, the probability-distribution calculating means comprises means for calculating, based on the calculated probability, a normal distribution of probability of the blood-pressure value of the living subject measured by the measuring device at the later time, and the range determining means comprises means for determining a modified blood-pressure range whose central value is equal to the modified blood-pressure value and within which the blood-pressure value of the living subject measured by the measuring device at the later time falls with the predetermined probability, and the apparatus further comprises period changing means for changing, when at least one of an upper limit value and a lower limit value of the determined blood-pressure range does not fall within a reference blood-pressure range, the predetermined period to a changed period shorter than the predetermined period, so that the measuring device measures a blood-pressure value of the living subject at the changed period; and period re-changing means for re-changing, when at least one of an upper limit value and a lower limit value of the modified blood-pressure range falls within the reference blood-pressure range after the predetermined period is changed to the changed period, the changed period back to the predetermined period, so that the measuring device measures a blood-pressure value of the living subject at the predetermined period. The fact that the upper and lower limit values of the modified BP range falls within the reference BP range after the predetermined period has been changed to the changed period means that the BP of the subject that has been predicted to go out of the reference BP range is now predicted not to go out of the reference BP range. Accordingly, the period re-changing means re-changes the changed period back to the predetermined period. Thus, the measuring device measures a BP value of the subject at the longer, predetermined period, which leads to relieving the subject of the burden of being measured at the shorter, changed period. However, the reference BP range may be replaced with a single reference BP value, according to the nineteenth or twentieth feature (19) or (20) described below.

(19) According to a nineteenth feature of the present invention that includes the seventeenth feature (17), the probability calculating means comprises means for calculating a probability with which a blood-pressure value of the living subject measured by the measuring device at the later time is equal to the modified blood-pressure value, according to the predetermined relationship between time and probability, the probability-distribution calculating means comprises means for calculating, based on the calculated probability, a normal distribution of probability of the blood-pressure value of the living subject measured by the measuring device at the later time, and the range determining means comprises means for determining a modified blood-pressure range whose central value is equal to the modified blood-pressure value and within which the blood-pressure value of the living subject measured by the measuring device at the later time falls with the predetermined probability, and the apparatus further comprises period changing means for changing, when at least one of an upper limit value and a lower limit value of the determined blood-pressure range is greater than a reference blood-pressure value, the predetermined period to a changed period shorter than the predetermined period, so that the measuring device measures a blood-pressure value of the living subject at the changed period; and period re-changing means for re-changing, when at least one of an upper limit value and a lower limit value of the modified blood-pressure range is not greater than the reference blood-pressure value after the predetermined period is changed to the changed period, the changed period back to the predetermined period, so that the measuring device measures a blood-pressure value of the living subject at the predetermined period.

(20) According to a twentieth feature of the present invention that includes the seventeenth feature (17), the probability calculating means comprises means for calculating a probability with which a blood-pressure value of the living subject measured by the measuring device at the later time is equal to the modified blood-pressure value, according to the predetermined relationship between time and probability, the probability-distribution calculating means comprises means for calculating, based on the calculated probability, a normal distribution of probability of the blood-pressure value of the living subject measured by the measuring device at the later time, and the range determining means comprises means for determining a modified blood-pressure range whose central value is equal to the modified blood-pressure value and within which the blood-pressure value of the living subject measured by the measuring device at the later time falls with the predetermined probability, and the apparatus further comprises period changing means for changing, when at least one of an upper limit value and a lower limit value of the determined blood-pressure range is smaller than a reference blood-pressure value, the predetermined period to a changed period shorter than the predetermined period, so that the measuring device measures a blood-pressure value of the living subject at the changed period; and period re-changing means for re-changing, when at least one of an upper limit value and a lower limit value of the modified blood-pressure range is not smaller than the reference blood-pressure value after the predetermined period is changed to the changed period, the changed period back to the predetermined period, so that the measuring device measures a blood-pressure value of the living subject at the predetermined period.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
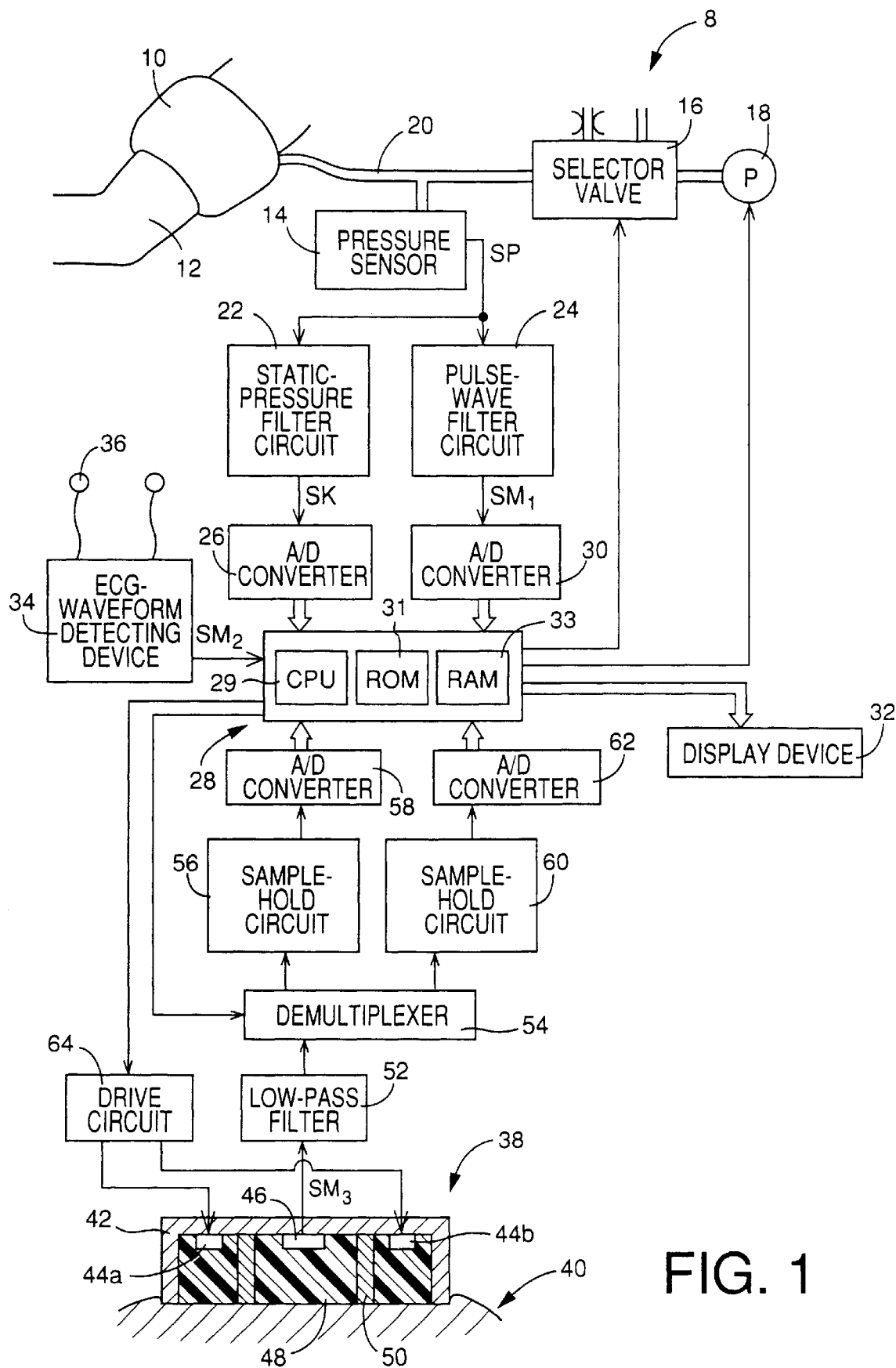
FIG. 1 is a diagrammatic view of a blood-pressure ("BP") monitoring apparatus embodying the present invention.

Referring to FIG. 1, there will be described a blood-pressure ("BP") monitoring apparatus 8 embodying the present invention.

In FIG. 1, the BP monitoring apparatus 8 includes an inflatable cuff 10 which includes a belt-like cloth bag and a rubber bag accommodated in the cloth bag and which is adapted to be wrapped around, e.g., an upper arm 12 of a patient as a living subject; and a pressure sensor 14, a selector valve 16, and an air pump 18 each of which is connected to the cuff 10 via piping 20. The selector valve 16 is selectively placed in a cuff-inflation position in which the selector valve 16 permits a pressurized air to be supplied from the air pump 18 to the cuff 10, a slow-deflation position in which the valve 16 permits the pressurized air to be slowly discharged from the cuff 10 into the atmosphere, and a quick-deflation position in which the valve 16 permits the pressurized air to be quickly discharged from the cuff 10 into the atmosphere.

The pressure sensor 14 detects an air pressure in the cuff 10, and supplies a pressure signal, SP, indicative of the detected pressure to each of a static-pressure filter circuit 22 and a pulse-wave filter circuit 24. The static-pressure filter circuit 22 includes a low-pass filter and extracts, from the pressure signal SP, a static component contained in the signal SP, i.e., a cuff-pressure signal, SK, indicative of the static cuff pressure. The cuff-pressure signal SK is supplied to an electronic control device 28 via an analog-to-digital ("A/D") converter 26. The pulse-wave filter circuit 24 includes a band-pass filter and extracts, from the pressure signal SP, an oscillatory component having predetermined frequencies, i.e., a pulse-wave signal, $SM_1$. The pulse-wave signal $SM_1$ is supplied to the control device 28 via an A/D converter 30. The pulse-wave signal $SM_1$ is indicative of the cuff pulse wave, i.e., oscillatory pressure wave which is produced from a brachial artery (not shown) of the patient in synchronism with the heartbeat of the patient and is propagated to the cuff 10.

The control device 28 is essentially provided by a so-called microcomputer including a central processing unit ("CPU") 29, a read only memory ("ROM") 31, a random access memory ("RAM") 33, and an input-and-output ("I/O") port (not shown). The CPU 29 processes signals according to control programs pre-stored in the ROM 31 by utilizing a temporary-storage function of the RAM 33, and supplies drive signals to the selector valve 16 and the air pump 18 via the I/O port.

The BP monitoring apparatus 8 further includes an electrocardiographic ("ECG") waveform detecting device 34 which continuously detects an ECG waveform indicative of the action potential of cardiac muscle of the patient, through a plurality of electrodes 36 being put on predetermined portions of the patient, and supplies an ECG-waveform signal, $SM_2$, indicative of the detected ECG waveform, to the control device 28. The ECG waveform detecting device 34 is used for detecting a Q-wave or an R-wave of the ECG waveform that corresponds to a time point when the outputting of blood from the heart of the patient toward the aorta is started. The ECG waveform detecting device 34 provides a first pulse-wave detecting device.

The BP monitoring apparatus 8 further includes a photoelectric-pulse-wave detecting probe 38 (hereinafter, referred to as the "probe" 38) which is employed as part of a pulse oximeter. The probe 38 functions as a peripheral-pulse-wave detecting device which detects a peripheral pulse wave propagated to a peripheral artery including capillaries. The probe 38 provides a second pulse-wave detecting device. The probe 38 is adapted to be set on a skin or a body surface 40 of the patient, e.g., an end portion of a finger of the patient, with the help of a band (not shown), such that the probe 38 closely contacts the body surface 40. The probe 38 includes a container-like housing 42 which opens in a certain direction; a first and a second group of light emitting elements 44a, 44b, such as light emitting diodes ("LEDs"), which are disposed on an outer peripheral portion of an inner bottom surface of the housing 42 (hereinafter, referred to as the light emitting elements 44 in the case where the first and second groups of light emitting elements 44a, 44b need not be discriminated from each other); a light receiving element 46, such as a photodiode or a phototransister, which is disposed on a central portion of the inner bottom surface of the housing 42; a transparent resin 48 which fills the housing 42 to cover the light emitting elements 44 and the light receiving element 46 provided therein; and an annular shading member 50 which is disposed between the light emitting elements 44 and the light receiving element 46, for preventing the lights emitted toward the body surface 40 by the light emitting elements 44 and reflected from the body surface 40 (not the body tissue), from being received by the light receiving element 46.

The first and second groups of light emitting elements 44a, 44b emit a red light having an about 660 nm wavelength and an infrared light having an about 800 nm wavelength, respectively. The first and second light emitting elements 44a, 44b alternately emit the red and infrared lights at a predetermined frequency. The lights emitted toward the body surface 40 by the light emitting elements 44 are reflected from the body tissue of the patient where dense capillaries are present, and the reflected lights are received by the common light receiving element 46. In place of the 660 nm and 800 nm wavelengths lights, the first and second light emitting elements 44a, 44b may emit any other pair of lights having different wavelengths, so long as one light of the pair exhibits significantly different absorption factors with respect to oxygenated hemoglobin and reduced hemoglobin, respectively, and the other light exhibits substantially the same absorption factors with respect to the two sorts of hemoglobin, i.e., has a wavelength which is reflected by each of the two sorts of hemoglobin.

The light receiving element 46 outputs, through a low-pass filter 52, a photoelectric-pulse-wave signal, $SM_3$, indicative of the amount of received light. The light receiving element 46 may be connected to the low-pass filter 52 via an amplifier or the like, if appropriate. The low-pass filter 52 removes, from the photoelectric-pulse-wave signal SM3 input thereto, noise having frequencies higher than that of the pulse wave, and outputs the noise-free signal $SM_3$, to a demultiplexer 54. The photoelectric pulse wave indicated by the signal $SM_3$ can be a volumetric pulse wave which is produced in synchronism with the pulse of the patient. Thus, the photoelectric pulse wave is a pulse-synchronous wave.

The demultiplexer 54 is switched according to signals supplied thereto from the control device 28 in synchronism with the alternate light emissions of the first and second light emitting elements 44a, 44b. Thus, the demultiplexer 54 successively supplies, to the I/O port (not shown) of the control device 28, an electric signal, $SM_R$, indicative of the red light through a first sample-and-hold circuit 56 and an A/D converter 58, and an electric signal, $SM_{IR}$, indicative of the infrared light through a second sample-and-hold circuit 60 and an A/D converter 62. The first and second sample-and-hold circuits 56, 60 hold the electric signals $SM_R$, $SM_{IR}$ input thereto, respectively, and do not output those electric signals to the A/D converters 58, 62, before the prior signals $SM_R$, $SM_{IR}$ are completely converted by the A/D converters 58, 62, respectively.

In the control device 28, the CPU 29 carries out a measuring operation according to control programs pre-stored in the ROM 31 by utilizing the temporary-storage function of the RAM 33. More specifically described, the CPU 29 generates a light-emit signal, SLV, to a drive circuit 64 so that the first and second light emitting elements 44a, 44b alternately emit the red and infrared lights at a predetermined frequency, respectively, such that each light emission lasts for a predetermined period. In synchronism with the alternate light emissions of the first and second light emitting elements 44a, 44b, the CPU 29 generates a switch signal, SC, to the demultiplexer 54 so as to correspondingly place the demultiplexer 54 in a first or a second position. Thus, the signals $SM_R$, $SM_{IR}$ are separated from each other by the demultiplexer 54 such that the signal $SM_R$ is supplied to the first sample-and-hold circuit 56 while the signal $SM_{IR}$ is supplied to the second sample-and-hold circuit 60. Moreover, the CPU 29 determines an oxygen saturation in the blood of the patient, based on respective amplitudes of the signals $SM_R$, $SM_{IR}$, according to a predetermined expression pre-stored in the ROM 31. The blood oxygen saturation determining method is disclosed in U.S. Pat. No. 5,131,391.

The BP monitoring apparatus 8 further includes a display device 32 which is connected to the control device 28. The CPU 29 of the control device 28 supplies electric if signals to the display device 32. The display device 32 includes a cathode ray tube ("CRT") and a speaker.

Figure 2:
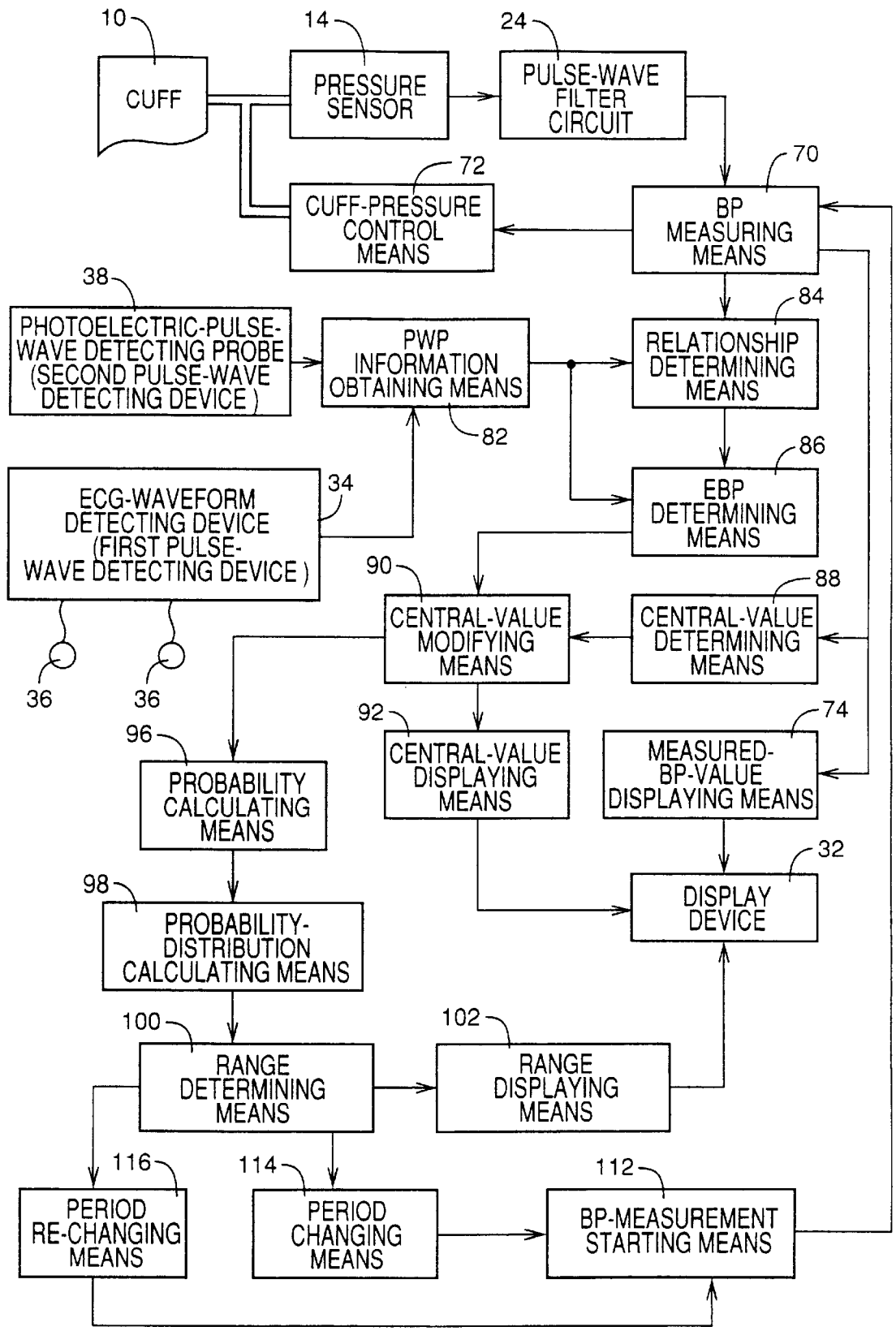
FIG. 2 is a block diagram illustrating essential functions of an electronic control device of the apparatus of FIG. 1.

FIG. 2 illustrates essential functions of the control device 28 of the present BP monitoring apparatus 8. A BP measuring means or circuit 70 measures a BP value of the patient, based on the variation of respective amplitudes of heartbeat-synchronous pulses of a pulse wave which is produced while a cuff-pressure control means or circuit 72 changes a pressing pressure of the inflatable cuff 10 being wrapped around the upper arm of the patient. More specifically described, the BP measuring means 70 measures a systolic, a mean, and a diastolic BP value, $BP_{SYS}$, $BP_{MEAN}$, $BP_{DIA}$, of the patient, according to a well-known oscillometric method, based on the variation of respective amplitudes of heartbeat-synchronous pulses of the pulse wave represented by the pulse-wave signal $SM_1$ obtained while the air pressure of the cuff 10 is slowly decreased at the rate of about 3 mmHg/sec after having been quickly increased up to a predetermined target pressure value, $P_{CM}$, (e.g., 180 mmHg).

Figure 3:
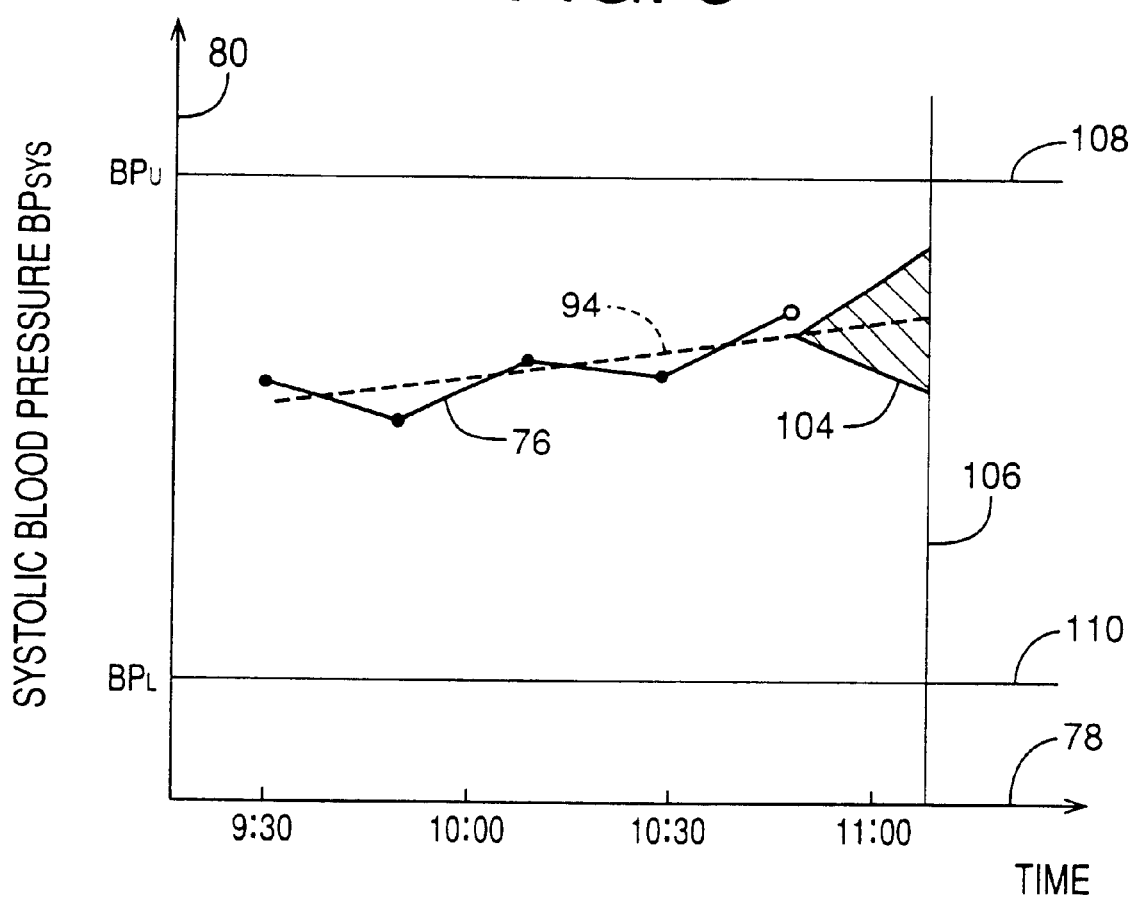
FIG. 3 is a view showing an example of a screen image which is displayed, on a display device of the apparatus of FIG. 1, when a BP value of a living subject is measured by a BP measuring device of the apparatus of FIG. 1.

A measured-BP-value displaying means or circuit 74 displays, in a two-dimensional coordinate system defined by a first axis 78 indicative of times when BP values of the patient are measured by the BP measuring means 70 and a second axis 80 indicative of BP values which are measured by the BP measuring means 70, a graph representing a time-wise trend of the BP values measured by the BP measuring means 70. The two-dimensional coordinate system is provided in the screen image displayed on the display device or CRT 32. A diagonal line 76, shown in FIG. 3, represents a time-wise trend of the systolic BP values $BP_{SYS}$ which are periodically measured by the BP measuring means 70 at a predetermined period, $T_{BP}$. FIG. 3 shows a screen image which is displayed on the display device 32 when each systolic BP value $BP_{SYS}$ of the patient is measured by the BP measuring means 70. The symbol "O" (white circle) indicates the current time.

Figure 4:
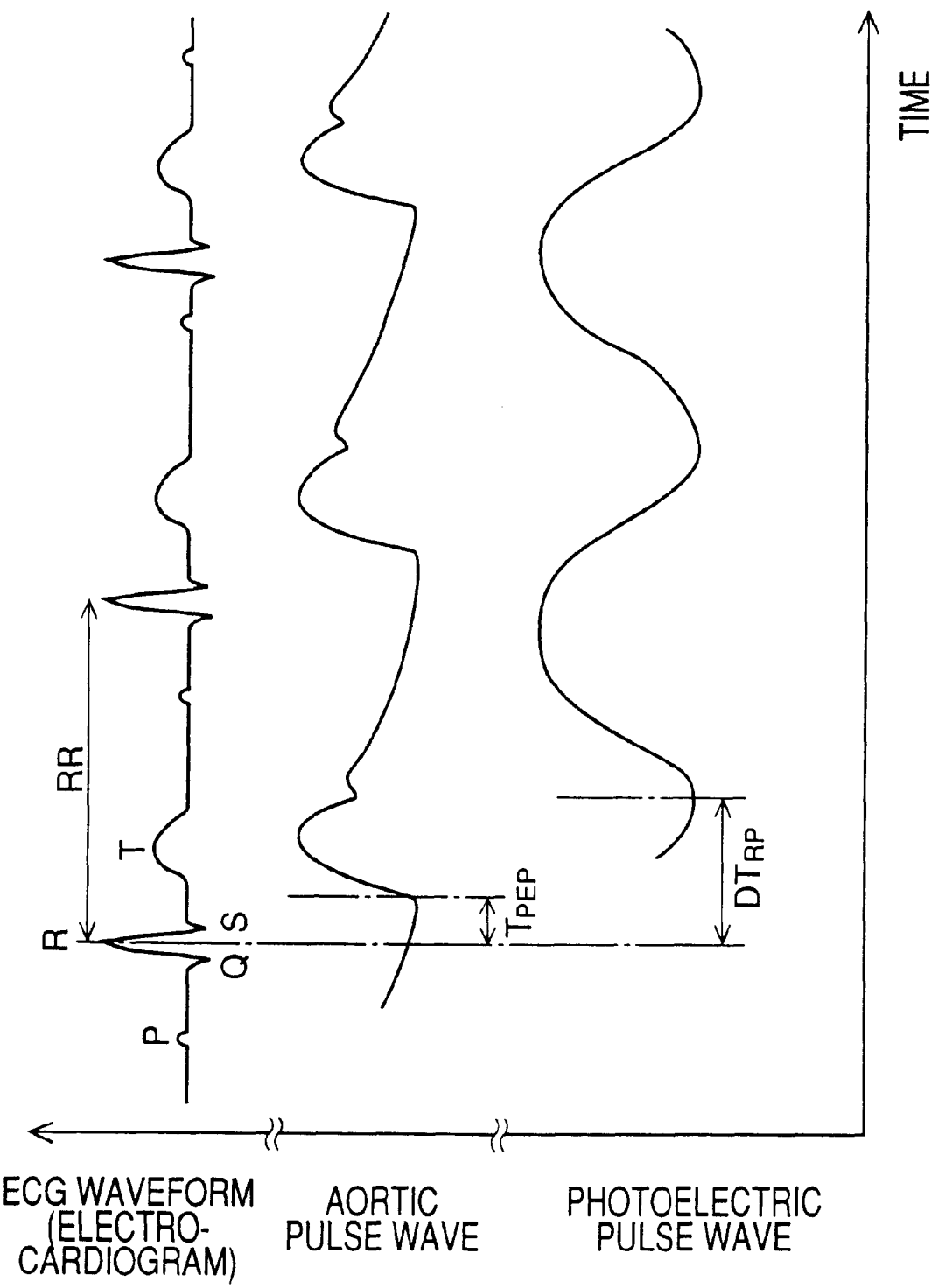
FIG. 4 is a view showing a time difference, $DT_{RP}$, which is obtained by the operation of the control device of FIG. 2.

A pulse-wave-propagation ("PWP") information obtaining means or circuit 82 obtains information, which relates to the propagation of a pulse wave which propagates through an artery of the patient, such as a time duration, which is needed for a pulse wave to propagate between two different portions of an artery. The PWP information obtaining means 82 includes a time-difference calculating means or circuit for iteratively calculating, as a pulsewave propagation time, $DT_{RP}$, a time difference between a predetermined point (e.g., R-wave) on the ECG waveform of each of periodic pulses iteratively detected by the ECG waveform detecting device 34 and a predetermined point (e.g., rising point, that is, minimum point) on the waveform of a corresponding one of periodic pulses of the photoelectric pulse wave detected by the probe 38, as shown in FIG. 4. The PWP information obtaining means 82 calculates, for every pair, every second pair, or every third pair, of periodic ECG pulse and periodic photoelectric pulse, a velocity, $V_M$ (m/sec), of the pulse wave propagating through the artery of the patient, based on a calculated propagation time $DT_{RP}$, according to the following expression (1) pre-stored in the ROM 31:

$$V_M = L/(DT_{RP} - T_{PEP}) \quad (1)$$

where

L (m) is a length of the artery as measured from the left ventricle via the aorta to the position where the probe 38 is set; and $T_{PEP}$ (sec) is a pre-ejection period between the R-wave of the ECG waveform of each pulse and the minimum point of the waveform of a corresponding pulse of an aortic pulse wave.

The values L, $T_{PEP}$ are constants, and are experimentally obtained in advance.

A relationship determining means or circuit 84 determines two coefficients, $\alpha$, $\beta$, in the following expression (2) or (3), based on two systolic BP values $BP_{SYS}$ measured by the BP measuring means 70 in two BP measuring operations, and two pulse-wave propagation time values $DT_{RP}$ or two pulse-wave propagation velocity values $V_M$. Each value $DT_{RP}$, $V_M$ may be an average of a plurality of values $DT_{RP}$, $V_M$ which are obtained before each BP measuring operation. The expressions (2) and (3) respectively define a relationship between pulse-wave propagation time $DT_{RP}$ and estimated BP value EBP, and a relationship between pulse-wave propagation velocity $V_M$ and estimated BP value EBP. In place of the relationship between either one of $DT_{RP}$ and $V_M$, and estimated systolic BP value $EBP_{SYS}$, a relationship between either one of $DT_{RP}$ and $V_M$, and estimated mean BP value $EBP_{MEAN}$, or a relationship between either one of $DT_{RP}$ and $V_M$, and estimated diastolic BP value $EBP_{DIA}$ may be employed. In short, the relationship determining means 84 determines the coefficients $\alpha$, $\beta$ of an appropriate one of the above-indicated relationships, depending upon which one of the estimated systolic, mean, and diastolic BP values $EBP_{SYS}$, $EBP_{MEAN}$, $EBP_{DIA}$ is selected as a monitored BP value.

$$EBP = \alpha(DT_{RP}) + \beta \quad (2)$$

where $\alpha$ is a negative constant, and $\beta$ is a positive constant.

$$EBP = \alpha(V_M) + \beta \quad (3)$$

where $\alpha$ and $\beta$ are positive constants.

Figure 9:
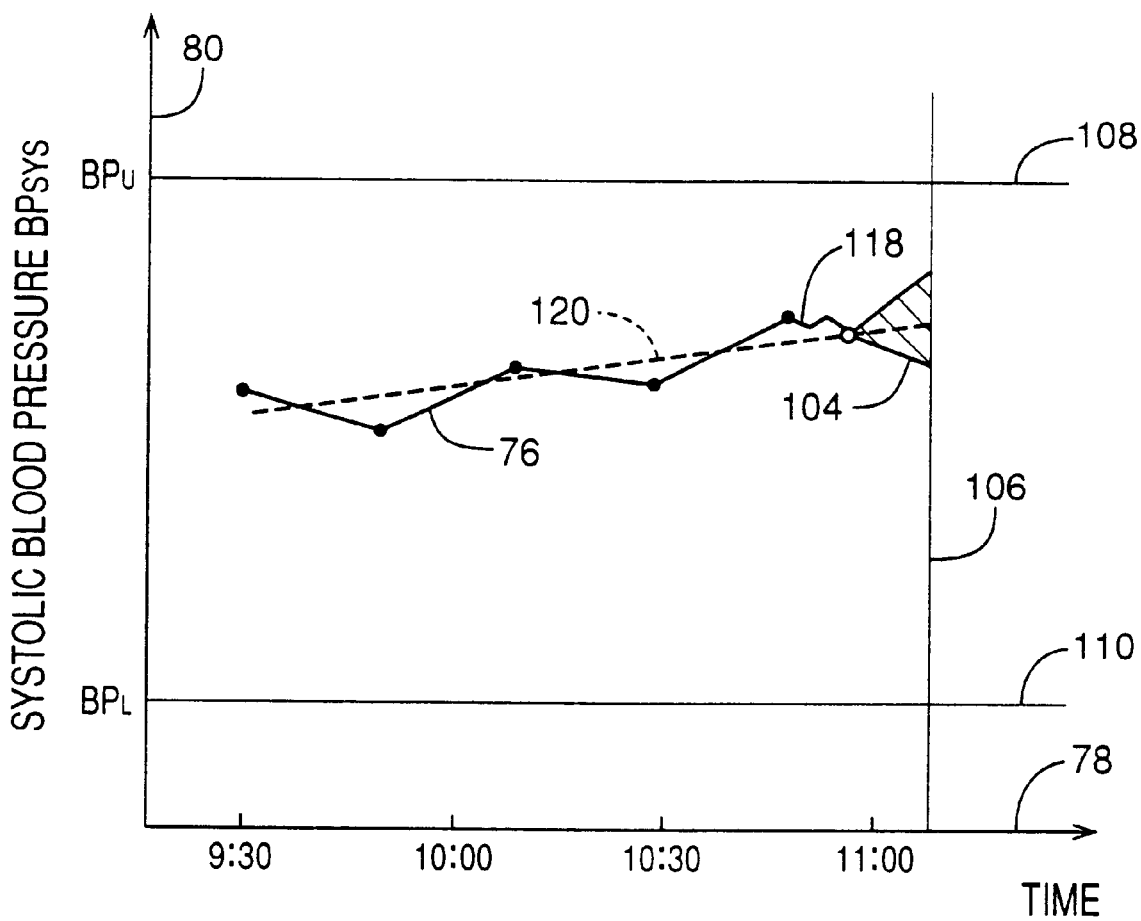
FIG. 9 is a view showing an example of a screen image which is displayed, on the display device of the apparatus of FIG. 1, when a BP value of the living subject is estimated by the control device of the apparatus of FIG. 1.

An EBP determining means or circuit 86 iteratively determines an EBP value of the patient, based on the actual pulse-wave propagation time $DT_{RP}$ or the actual pulse-wave propagation velocity $V_M$ iteratively obtained by the PWP information obtaining means 82, according to the above-indicated relationship represented by the second or third expression (2) or (3). FIG. 9 shows a graph 118 representing a time-wise trend of the estimated systolic BP values $EBP_{SYS}$ determined by the EBP determining means 86.

A central-value determining means or circuit 88 determines, based on a plurality of BP values measured by the BP measuring means 70 in a plurality of BP measuring operations including the last (i.e., current) BP measuring operation, a central value, PBP0, of a predicted BP ("PBP") range within which a BP value of the patient is predicted to fall at a later time (e.g., at the time of the next BP measuring operation) by a predetermined time (e.g., a time equal to the predetermined period $T_{BP}$, e.g., 20 minutes) from when the last or current BP value is measured by the BP measuring means 70 in the last or current BP measuring operation. The central value PBP0 is a predicted BP ("PBP") value which is predicted to be measured, with the greatest probability, by the BP measuring means 70 at the later time. For example, the central-value determining means 88 determines, by using the method of least squares, a straight broken line 94 (FIG. 3) approximating a time-wise change of the systolic BP values $BP_{SYS}$ measured by the BP measuring means 70, and determines, based on the straight broken line 94, the central value PBP0 which is predicted to be most probably measured by the BP measuring means 70 at the later time.

A central-value modifying means or circuit 90 modifies the central value PBP0 determined by the central-value determining means 88, based on the EBP value or values determined by the EBP determining means 78. More specifically described, the central-value modifying means 90 determines a modified central value PBP0' based on not only the BP values measured by the BP measuring means 70 but also one or more EBP values determined by the EBP determining means 86. For example, like the central-value determining means 88, the central-value modifying means 90 determines, by using the method of least squares, a straight broken line 120 (FIG. 9) approximating a time-wise change of the systolic BP values $BP_{SYS}$ measured by the BP measuring means 70 and the estimated systolic BP values $EBP_{SYS}$ determined by the EBP determining means 86, and determines, based on the straight broken line 120, the modified central value PBP0' which is predicted to be most probably measured by the BP measuring means 70 at the later time.

A central-value displaying means or circuit 92 displays, on the two-dimensional coordinate system provided in the screen image displayed on the display device 32, the straight broken line 94 (FIG. 3) representing the central value PBP0 determined by the central-value determining means 88, or the straight broken line 120 (FIG. 9) representing the modified central value PBP0' determined by the central-value modifying means 90, together with the diagonal line 76 representing the time-wise trend of the BP values measured by the BP measuring means 70. Each of the straight broken line 94 (FIG. 3) and the straight broken line 120 (FIG. 9) ends at the time of the next BP measuring operation, that is, a time, indicated by a vertical line 106, which is later by the predetermined period TBP than the time of the last or current BP measuring operation, indicated by the symbol "O" at the end of the diagonal line 76. Thus, the end of the straight broken line 94 represents the central value PBP0 at the later time indicated by the vertical line 106, and the end of the straight broken line 120 represents the modified central value PBP0' at the same later time.

A probability calculating means or circuit 96 calculates a probability, $P_{PBP0}$, with which a BP value of the patient that will be measured by the BP measuring means 70 at the later time is equal to the central value PBP0 determined by the central-value determining means 88, or the modified central value PBP0' determined by the central-value modifying means 90, according to a predetermined relationship between time, t, and probability $P_{PBP0}$, defined by the following expression (4):

$$P_{PBP0}=a^t (0<a<1) \quad (4)$$

where t is a later time measured from the time of the current BP measuring operation, indicated by the symbol "O" at the end of the diagonal line 76; and a is a constant.

Figure 5:
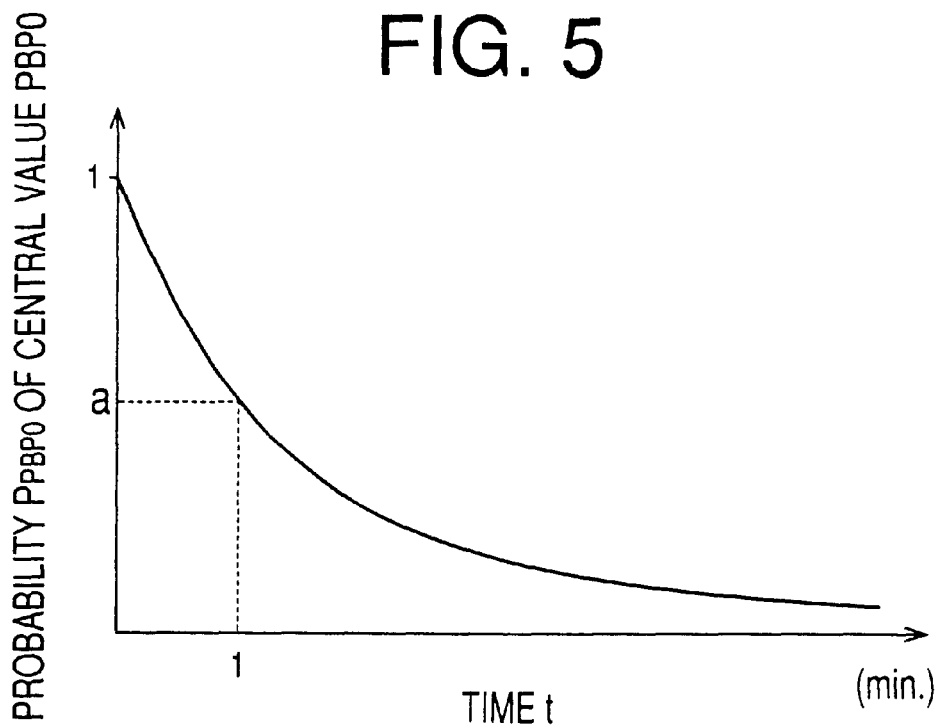
FIG. 5 is a view showing a predetermined relationship between time, t, and probability, $P_{PBPO}$.

The constant a is empirically obtained, in advance, in such a manner that assuming that the BP measuring means 70 will measure a BP value of the patient at a time one minute later than the time of the last or current BP measuring operation, the BP value measured at the one-minute later time by the BP measuring means 70 is predicted to be equal to the determined central value PBP0 with a probability equal to the constant a. Therefore, the probability $P_{PBP0}$ monotonously decreases as the time t passes, as shown in FIG. 5. A single constant a may be used for all patients or all sorts of diseases, or an appropriate one may be selected and used from a plurality of different constants a, depending upon each individual patient, or a particular sort of disease of each patient.

Figure 6:
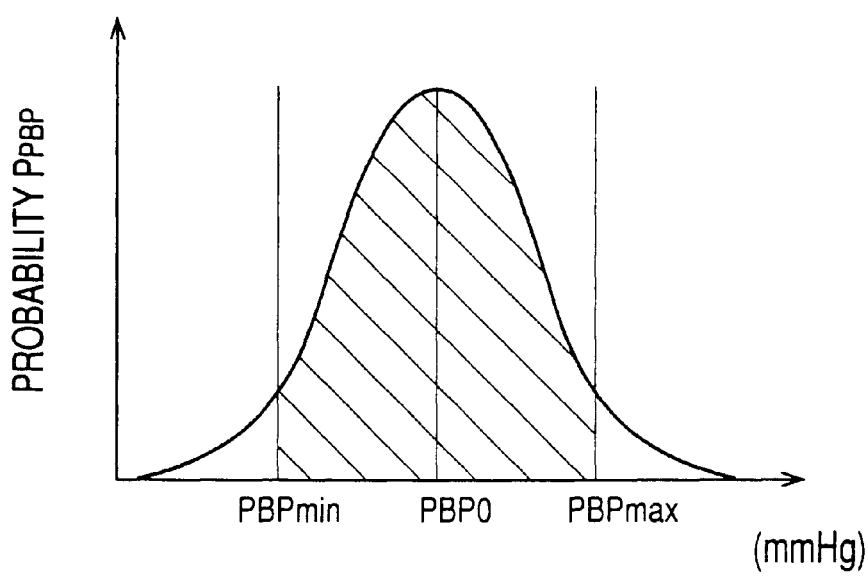
FIG. 6 is a view showing a normal distribution of probability $P_{PBP}$ which is calculated by a probability-distribution calculating means or circuit of the control device of FIG. 2.

A probability-distribution calculating means or circuit 98 calculates, based on the probability $P_{PBP0}$ calculated by the probability calculating means 96, a distribution of probability, $P_{PBP}$, of a predicted BP ("PBP") value of the patient which is predicted to be measured by the BP measuring means 70 at the later time, on the assumption that the distribution of probability $P_{PBP}$ of the PBP value of the patient at the later time is a normal distribution whose central or average value is equal to the probability $P_{PBP0}$. As described above, the probability $P_{PBP0}$ of the central value PBP0 at the later time can be obtained, according to the above-indicated expression (4), such that $P_{PBP0}=a^t$. The following expression (5) defines a general formula for a normal distribution. Therefore, the following expression (6) is obtained by assuming in the expression (5) that x (parameter)=m (average) and $P=a^t$. A standard deviation, σ, of the normal distribution of probability $P_{PBP}$ of the PBP value of the patient at the later time can be obtained from the expression (6). The central or average probability $P_{PBP0}$ and the standard deviation σ cooperate with each other to define the normal distribution of probability $P_{PBP0}$ of the PBP value at the later time t. From the condition of 0<a<1, the expression (6) indicates that as the time t increases, the standard deviation σ increases, that is, the curve representing the distribution of probability $P_{PBP}$ of the PBP value at the later time becomes flatter. FIG. 6 shows an example of a normal distribution of probability $P_{PBP}$ which is calculated by the probability-distribution calculating means 98.

$$P=\{1/\sqrt{(2\pi)}\sigma\}\exp\{-(x-m)^2/2\sigma^2\} \quad (5)$$

where m is an average; and

σ is a standard deviation.

$$a^t=\{1/\sqrt{(2\pi)}\sigma\} \quad (6)$$

A range determining means or circuit 100 determines a PBP range whose central value is equal to the central value PBP0 determined by the central-value determining means 88 and within which a BP value of the patient, which will be measured by the BP measuring means 70 at the later time, is predicted to fall with a predetermined probability (e.g., 90%), or a modified PBP range whose central value is equal to the modified central value PBP0' determined by the central-value modifying means 90 and within which the BP value of the patient which will be measured by the BP measuring means 70 at the later time is predicted to fall with the predetermined probability. FIG. 6 shows an example of the PBP range which has an upper limit value, $PBP_{max}$, and a lower limit value, $PBP_{min}$, and within which a BP value of the patient which will be measured by the BP measuring means 70 at a later time is predicted to fall with the probability of 90%.

A range displaying means or circuit 102 displays, on the two-dimensional coordinate system provided in the screen image displayed on the display device 32, a graph representing the PBP range, or the modified PBP range, determined by the range determining means 100, together with the diagonal line 76 representing the time-wise trend of the BP values measured by the BP measuring means 70 and either the straight broken line 94 (FIG. 3) representing the central value PBP0 determined by the central-value determining means 88 or the straight broken line 120 (FIG. 9) representing the modified central value PBP0' determined by the central-value modifying means 90.

For example, FIG. 3 shows a triangular area 104 representing a PBP range which is determined by the range determining means 100 in such a manner that a BP value of the patient measured by the BP measuring means 70 at a later time is predicted to fall with the probability of 90% within the determined PBP range. The left-hand angle of the triangular area 104 is equally divided by the broken straight line 94 representing the central value PBP0. A dimension or length of the triangular area 104 as measured in a direction parallel to the vertical axis indicative of systolic BP, at an arbitrary time on the horizontal axis indicative of time, represents a PBP range within which a BP value of the patient measured by the BP measuring means 70 at that time is predicted to fall with the probability of 90%. In the graph shown in FIG. 3, reference numeral 108 designates an upper reference line representing an upper limit value, $BP_U$, of a predetermined normal BP range, and reference numeral 110 designates a lower reference line representing a lower limit value, $BP_L$, of the normal BP range. In the graph of FIG. 3, the PBP range represented by the triangular area 104 at the later time indicated by the vertical line 106 falls within the normal BP range. Therefore, the control device 28 predicts that the BP of the patient will not increase or decrease out of the normal BP range till the next BP measuring operation, i.e., the time later by the predetermined period $T_{BP}$.

A BP-measurement starting means or circuit 112 controls the BP measuring means 70 to periodically start a BP measuring operation at the predetermined period $T_{BP}$, e.g., 20 minutes.

A period changing means or circuit 114 changes the predetermined period $T_{BP}$ into a changed period, $T_{BP'}$ (e.g., 10 minutes) shorter than the initial period $T_{BP}$, when at least one of an upper and a lower limit value of a PBP range or a modified PBP range does not fall within the predetermined normal BP range, for example, when at least one of the upper and lower limit values $PBP_{max}$, $PBP_{min}$ of the PBP range shown in FIG. 6 does not fall within the predetermined normal BP range having the upper and lower limit values $BP_U$, $BP_L$ shown in FIG. 3.

A period re-changing means or circuit 116 re-changes, when at least one of an upper limit value and a lower limit value of a modified PBP range determined by the range determining means 100 falls within the predetermined normal BP range after the predetermined period $T_{BP}$ is changed to the changed period $T_{BP'}$, the changed period $T_{BP'}$ back to the initial period $T_{BP}$.

Next, there will be described the operation of the control device 28 of the BP monitoring apparatus 8 by reference to the flow charts of FIGS. 7 and 8. The flow chart of FIG. 7 represents the BP measuring routine which is basically periodically carried out at the predetermined period $T_{BP}$, and the flow chart of FIG. 8 represents the EBP determining routine which is carried out in response to each heartbeat of the patient during an interval of time between each pair of successive BP measuring operations carried out at the predetermined period $T_{BP}$.

Figure 7:
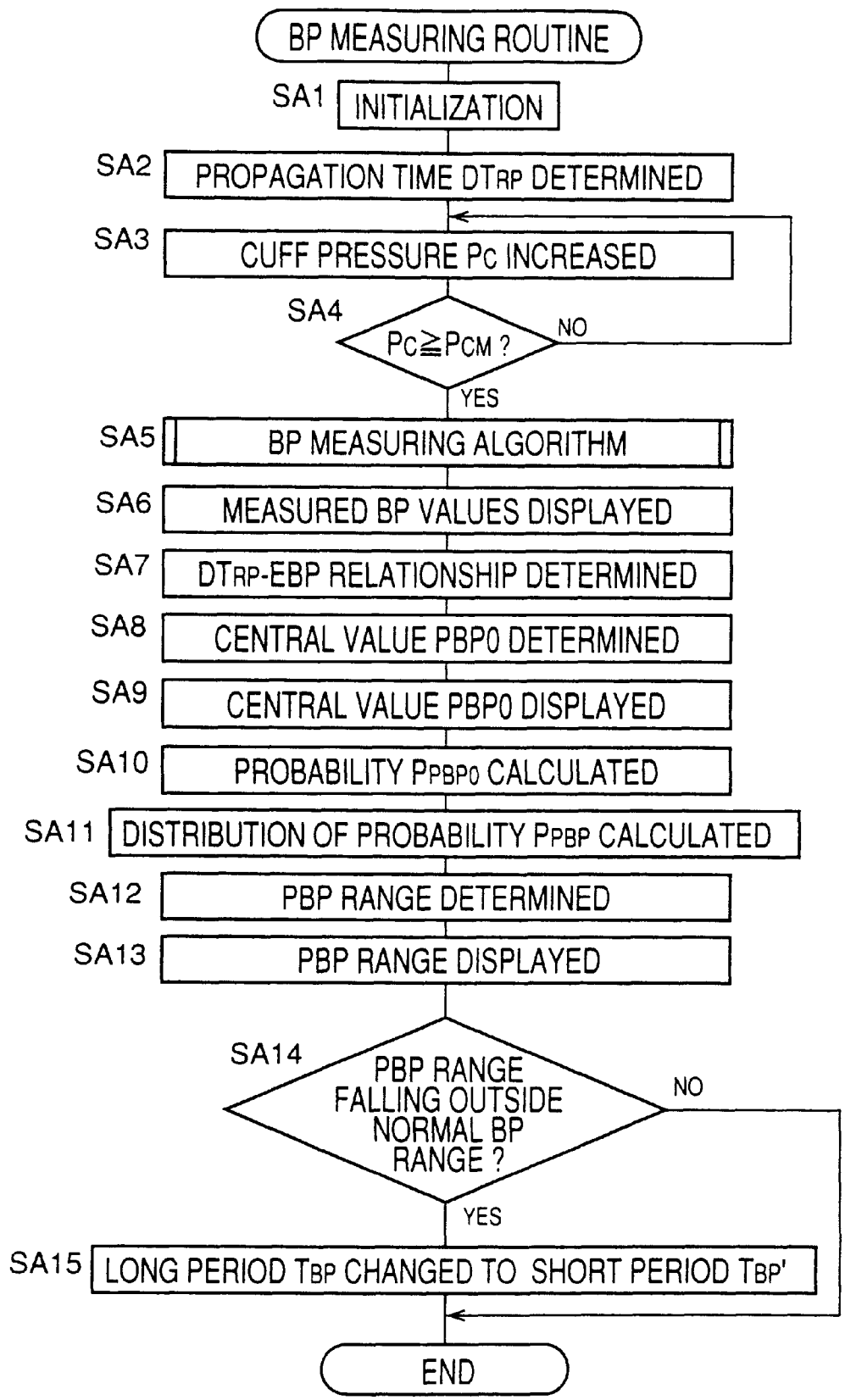
FIG. 7 is a flow chart representing a BP measuring routine according to which the control device of the apparatus of FIG. 1 is operated for measuring a BP value of the living subject.
Figure 8:
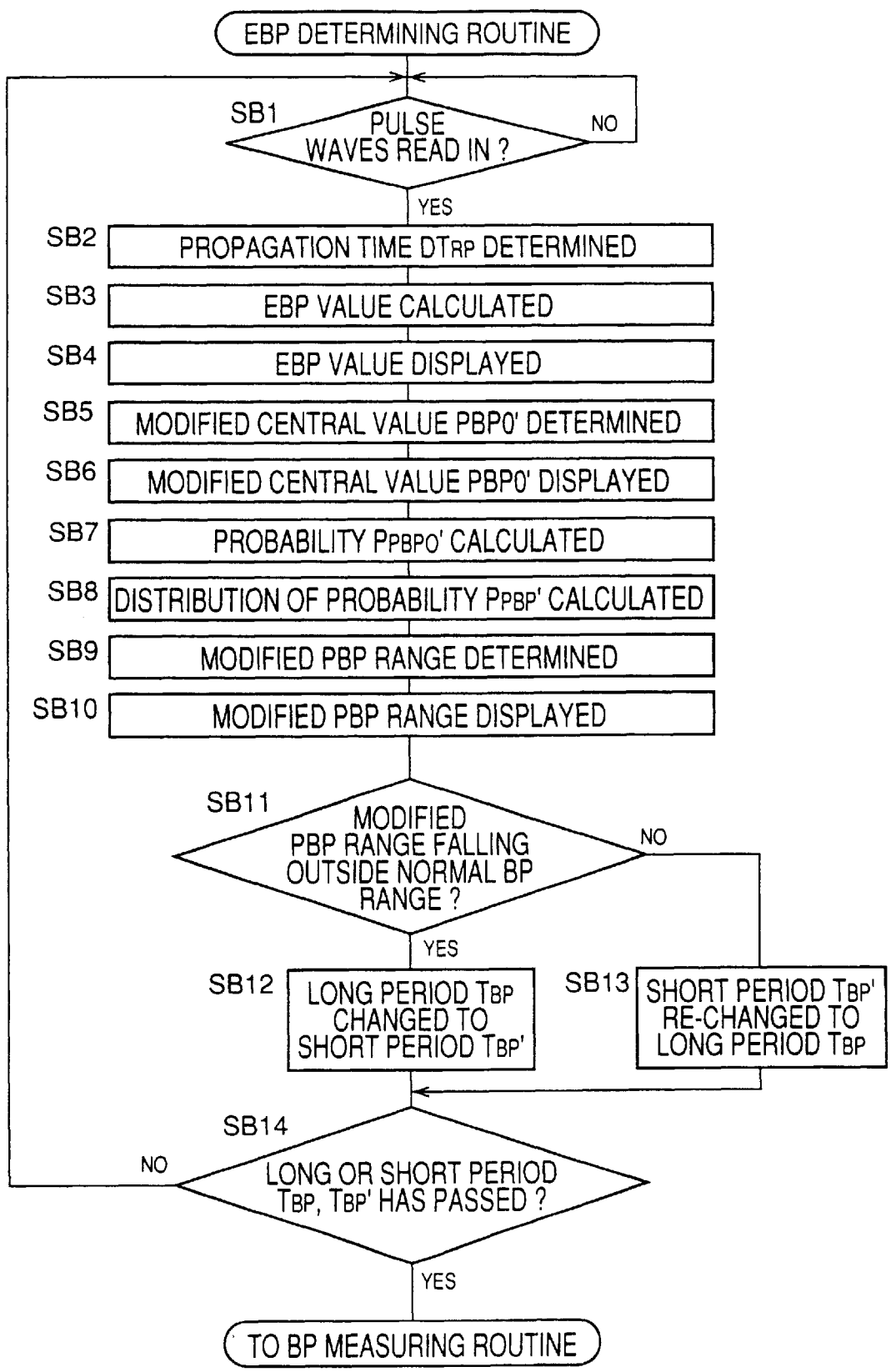
FIG. 8 is a flow chart representing a BP estimating routine according to which the control device of the apparatus of FIG. 1 is operated for estimating a BP value of the living subject.

The control of the CPU 29 begins with Step SA1 of the flow chart of FIG. 7, where a timer, register, etc. (not shown) are reset. Step SA1 is followed by Step SA2 to calculate, as a pulse-wave propagation time $DT_{RP}$, a time difference between an R-wave of the ECG waveform of a pulse and a rising or minimum point of the waveform of a corresponding pulse of the photoelectric pulse wave which pulses are obtained immediately before the increasing of the cuff pressure. Step SA2 corresponds to the pulse-wave-propagation information obtaining means 82.

The control of the CPU 29 goes to Steps SA3 and SA4 corresponding to the cuff-pressure control means 72. At Step SA3, the CPU 29 quickly increases the cuff pressure for a BP measurement, by switching the selector valve 16 to the inflation position and operating the air pump 18. Step SA3 is followed by Step SA4 to judge whether or not the cuff pressure $P_C$ is equal to or greater than a predetermined target value $P_{CM}$ (e.g., 180 mmHg). If a negative judgement is made at Step SA4, the control of the CPU 29 goes back to Step SA2 and continues increasing the cuff pressure $P_C$.

On the other hand, if a positive judgement is made at Step SA4, the control of the CPU 29 goes to Step SA5 to carry out a BP measuring algorithm. More specifically described, the air pump 18 is stopped and the selector value 16 is switched to the slow-deflation position where the selector valve 16 permits the pressurized air to be slowly discharged from the cuff 10. A systolic BP value $BP_{SYS}$, a mean BP value $BP_{MEAN}$, and a diastolic BP value $BP_{DIA}$ are determined, according to a well known oscillometric BP determining algorithm, based on the variation of respective amplitudes of heartbeat-synchronous pulses of the pulse wave represented by the pulse-wave signal $SM_1$ obtained while the cuff pressure is slowly decreased at a predetermined rate of about 3 mmHg/sec. Then, the selector valve 16 is switched to the quick-deflation position where the selector valve 16 permits the pressurized air to be quickly discharged from the cuff 10. Step SA5 corresponds to the BP measuring means 70. Step SA5 is followed by Step SA6 where the thus measured BP values, including the systolic BP value $BP_{SYS}$ indicated by the diagonal line 76 in the graph of FIG. 3, are displayed on the display device 32. If the thus measured BP values includes an abnormal BP value which does not fall within the predetermined normal BP range shown in FIG. 3 or FIG. 9, the speaker (not shown) of the display device 32 generates an alarm sound.

Next, Step SA6 is followed by Step SA7 to determine a pulse wave propagation information-estimated blood pressure relationship, based on two pulse-wave propagation time values $DT_{RP}$ calculated at Step SA2 in the last two control cycles each according to the flow chart of FIG. 7 and two systolic, mean, or diastolic BP values $BP_{SYS}$, $BP_{MEAN}$, $BP_{DIA}$ measured at Step SA5 in the last two control cycles including the last or current control cycle. More specifically described, after the systolic, mean, and diastolic BP values $BP_{SYS}$, $BP_{MEAN}$, $BP_{DIA}$ are measured at Step SA5, the relationship (i.e., the expression (2)) between pulse-wave propagation time $DT_{RP}$ and estimated BP value EBP is determined at Step SA7, based on the two BP values $BP_{SYS}$, $BP_{MEAN}$, or $BP_{DIA}$, and the two pulse-wave propagation time values $DT_{RP}$. Step SA7 corresponds to the pulse wave propagation information-estimated blood pressure relationship determining means 84. In addition, At Step SA7, the CPU 29 determines an estimated BP value EBP of the patient at the time of the last or current BP measuring operation, based on the pulse-wave propagation time value $DT_{RP}$ calculated at Step SA2, according to the thus determined relationship, i.e., the expression (2).

At Step SA8, the CPU 29 applies the method of least squares to a plurality of (e.g., five) systolic BP values $BP_{SYS}$ (or mean or diastolic BP values $BP_{MEAN}$ or $BP_{DIA}$) which have been measured at Step SA5 in the last five successive control cycles each according to the BP measuring routine of FIG. 7, and determines a straight line approximating the five systolic BP values $BP_{SYS}$. The thus determined straight line represents a central value PBP0 of a predicted BP ("PBP") range within which a systolic BP value of the patient is predicted to fall at a later time. Step SA8 corresponds to the central-value determining means 88. Step SA8 is followed by Step SA9 where the CPU 29 displays, in the two-dimensional coordinate system provided in the screen image displayed on the display device 32, the straight broken line 94, shown in FIG. 3, which represents the straight line determined at Step SA8 and which ends at the time of the next BP measuring operation indicated by the vertical line 106. A portion or length of the broken line 94 between the current BP measuring operation and the next one represents a central value PBP0 of a predicted BP range at an arbitrary time between the two BP measuring operations. Step SA9 corresponds to the central-value displaying means 92.

At Step SA10, the CPU 29 calculates, according to the predetermined relationship represented by the expression (4), the probability $P_{PBP0}$ $(=a^r)$ with which the BP value measured by the measuring means 70 in the next BP measuring operation is equal to the central value PBP0. Step SA10 corresponds to the probability calculating means 96. Step SA10 is followed by Step SA11 where the CPU 29 replaces the probability, P, in the expression (5) with the probability $P_{PBP0}$ $(=a^r)$ calculated at Step SA10, and thus obtains the standard deviation, σ. In addition, the CPU 29 determines, based on the probability $P_{PBP0}$ and the standard deviation σ, a distribution of probability $P_{PBP}$ of the predicted BP ("PBP") value of the patient at the time of the next BP measuring operation. Step SA11 corresponds to the probability-distribution calculating means 98.

At Step SA12, the CPU 29 determines, based on the distribution of probability $P_{PBP}$ calculated at Step SA11, a predicted-BP ("PBP") range whose central value is equal to the central value PBP0 and within which the BP value of the patient measured by the measuring means 70 in the next BP measuring operation is predicted to fall with a predetermined probability, e.g., 90%. For example, the CPU 29 determines the PBP range, shown in FIG. 6, which is defined by the upper and lower limit values $PBP_{max}$, $PBP_{min}$ and whose central value is equal to the central value PBP0. A value obtained by integrating a portion of the distribution curve $P_{PBP}$ between the upper and lower limit values $PBP_{max}$, $PBP_{min}$ is equal to 0.9. Step SA12 corresponds to the range determining means 100.

Step SA12 is followed by SA13 where the CPU 29 displays, in the coordinate system provided in the screen image on the display device 32, the triangular area 104 representing the PBP range determined at Step SA12. As the time t increases, the PBP range determined at Step SA12 becomes wider. Therefore, as the time t increases from the current time indicated by the symbol "O" in FIG. 3, the length or dimension of the triangular area 104 as measured along the vertical axis 80 becomes greater. Step SA13 corresponds to the range displaying means 102.

At Step SA14, the CPU 29 judges whether at least one of the upper and lower limit values $PBP_{max}$, $PBP_{min}$ of the PBP range at the time of the next BP measuring operation, determined at Step SA12, falls outside the upper and/or lower limit value $BP_U$, $BP_L$ of the predetermined normal BP range. If a negative judgment is made at Step SA14, the CPU 29 terminates the BP measuring routine of FIG. 7, without changing the predetermined period $T_{BP}$, and carries out the EBP determining routine of FIG. 8 in the state in which the predetermined period $T_{BP}$ is kept at its initial value, e.g., 20 minutes. On the other hand, if a positive judgment is made at Step SA14, it is predicted that the BP of the patient will go out of the normal BP range at the time of the next BP measuring operation, i.e., at the time after the predetermined period $T_{BP}$. The control of the CPU 29 goes to Step SA15 where the CPU 29 changes the predetermined period $T_{BP}$ to a shorter period $T_{BP'}$, e.g., 10 minutes. Then, the CPU 29 terminates the BP measuring routine of FIG. 7 and carries out the EBP determining routine of FIG. 8. Steps SA14 and SA15 correspond to the period changing means 114.

Next, the EBP determining routine will be described by reference to the flow chart of FIG. 8. First, at Step SB1, the CPU 29 judges whether or not the R-wave of the ECG waveform of a heartbeat-synchronous pulse and the waveform of a corresponding pulse of the photoelectric pulse wave have been read in from the ECG waveform detecting device 34 and the probe 38. If a negative judgment is made at Step SB1, the control of the CPU 29 waits until a positive judgment is made at Step SB1. If a positive judgment is made at Step SB1, the control of the CPU 29 goes to Step SB2 corresponding to the pulse-wave-propagation information obtaining means 82. At Step SB2, the CPU 29 calculates a pulse-wave propagation time $DT_{RP}$ based on the R-wave of the ECG waveform and the waveform of the photoelectric pulse wave read in at Step SB1, in the same manner as carried out at Step SA2.

Step SB2 is followed by Step SB3 corresponding to the estimated BP ("EBP") determining means 86. At Step SB3, the CPU 29 determines an estimated BP value EBP (i.e., an estimated systolic, mean, or diastolic BP value), based on the pulse-wave propagation time $DT_{RP}$ calculated at Step SB2, according to the pulse wave propagation information-estimated blood pressure relationship determined at Step SA7. Step SB3 is followed by Step SB4 where the CPU 29 displays, in the two-dimensional coordinate system provided in the screen image on the display device 32, a trend graph of the estimated BP values EBP determined for respective heartbeat-synchronous pulses of the ECG waveform and the photoelectric pulse wave. FIG. 9 shows a diagonal line 118 which is extended from the diagonal line 76 representing the last systolic BP value BP measured at Step SA5, and which represents the estimated systolic BP values $EBP_{SYS}$ determined at Step SB3 in successive control cycles each according to the flow chart of FIG. 8.

At Step SB5, the CPU 29 applies the method of least squares to the last five BP values measured at Step SA5 in the last five successive control cycles each according to the BP measuring routine of FIG. 7, and one or more EBP values determined at Step SB3 in one or more control cycles each according to the EBP determining routine of FIG. 8, and determines a straight line approximating the measured BP values and the determined EBP value or values. Thus, the straight line determined at Step SA8 is modified based on the EBP value or values determined at Step SB3. The thus modified straight line represents a modified central value PBP0' of a modified PBP range within which a systolic BP value of the patient is predicted to fall at a later time. Step SB5 corresponds to the central-value modifying means 90. Step SB5 is followed by Step SB6 where the CPU 29 displays, in the two-dimensional coordinate system provided in the screen image on the display device 32, the straight broken line 120, shown in FIG. 9, which represents the straight line determined at Step SB5 and which ends at the time of the next BP measuring operation indicated by the vertical line 106. A portion or length of the broken line 120 between the current and next BP measuring operations represents a modified central value PBP0' of a predicted BP range at an arbitrary time between the two BP measuring operations. Step SB6 corresponds to the central-value displaying means 92.

At Step SB7, the CPU 29 calculates, according to the predetermined relationship represented by the expression (4), the probability $P_{PBP0}$ (=a') with which the BP value measured by the measuring means 70 in the next BP measuring operation is equal to the modified central value PBP0'. Step SB7 corresponds to the probability calculating means 96. Step SB7 is followed by Step SB8 similar to Step SA11. Step SB8 corresponds to the probability-distribution calculating means 98. At Step SB9, the CPU 29 determines, based on the distribution of probability $P_{PBP}$ calculated at Step SB8, a modified PBP range whose central value is equal to the modified central value PBP0' and within which the BP value of the patient measured by the measuring means 70 in the next BP measuring operation is predicted to fall with the predetermined probability, e.g., 90%. Step SB9 corresponds to the range determining means 100. Step SB9 is followed by Step SB10 where the CPU 29 displays, in the coordinate system provided in the screen image on the display device 32, the triangular area 104 representing the modified PBP range determined at Step SB9. Step SB10 corresponds to the range displaying means 102.

At Step SB11, the CPU 29 judges whether at least one of an upper and a lower limit value $PBP_{max}$, $PBP_{min}$ of the modified PBP range at the time of the next BP measuring operation, determined at Step SB9, falls outside the upper and/or lower limit value $BP_U$, $BP_L$ of the normal BP range. If a positive judgment is made at Step SB11, it is predicted that the BP of the patient will go out of the normal BP range at the time of the next BP measuring operation, i.e., at the time after the predetermined period $T_{BP}$. In this case, the control of the CPU 29 goes to Step SB12 where the CPU 29 changes the predetermined period $T_{BP}$ to a shorter period $T_{BP'}$, e.g., 10 minutes, like at Step SA15. However, in the case where the predetermined period $T_{BP}$ has already been changed to the short period $T_{BP'}$ in a prior control cycle according to the routine of FIG. 8, the short period $T_{BP'}$ is maintained. Step SB12 corresponds to the period changing means 114.

On the other hand, if a negative judgment is made at Step SB11, the control of the CPU 29 goes to Step SB13 where the CPU 29 re-changes the changed, short period $T_{BP'}$ to the initial, long period $T_{BP}$, e.g., 20 minutes. However, in the case where the short period $T_{BP'}$ has already been re-changed to the long period $T_{BP}$ in a prior control cycle according to the routine of FIG. 8, the long period $T_{BP}$ is maintained. Step SB13 corresponds to the period re-changing means 116.

At Step SB14, the CPU 29 judges whether or not the timer which was reset to zero at Step SA1 has measured the predetermined period $T_{BP}$ which may have been changed to the short period $P_{BP'}$ at Step SB12, or further re-changed to the initial long period $T_{BP}$ at Step SB13. Step SB14 corresponds to the BP-measurement starting means 112. If a negative judgment is made at Step SB14, the control of the CPU 29 goes back to Step SB1 and the following steps so as to carry out the EBP determining routine, that is, determine an estimated BP value EBP for each pulse, and timewise display, on the display device 32, the trend graph of the determined estimated BP values EBP. On the other hand, if a positive judgment is made at Step SB14, the control of the CPU 29 terminates the EBP determining routine of FIG. 8 and goes back to the BP measuring routine of FIG. 7.

As is apparent from the foregoing description of the BP monitoring apparatus 8, the central-value determining means 88 determines, based on the BP values measured by the BP measuring means 70, the central value PBP0 of the PBP range within which the BP value of the patient, which will be measured by the BP measuring means 70 at the time of the next BP measuring operation, i.e., at the time later by the predetermined period $T_{BP}$ than the time of the last (i.e., current) BP measuring operation, is predicted to fall. In other words, the central value PBP0 is the BP value which is predicted to be most probably measured by the BP measuring means 70 at the time of the next BP measuring operation. In addition, the portion of the straight broken line 94 (FIG. 3) that corresponds to the interval between the last and next BP measuring operations represents a BP value which is predicted to be most probably measured by the BP measuring means 70 at an arbitrary time in the interval. The central value PBP0 is represented by the future-side end of the broken line 94 indicated by the vertical line 106. In view of the broken line 94, a medical person who attends to the patient can quickly give necessary treatments to the patient.

In addition, in the BP monitoring apparatus 8, the range determining means 100 determines, based on the distribution of probability $P_{PBP}$ determined by the probability-distribution calculating means 98, a PBP range whose central value is equal to the central value PBP0 and within which the BP value of the patient which will be measured by the BP measuring means 70 at the time of the next BP measuring operation is predicted to fall with the predetermined probability (e.g., 90%). The triangular area 104 shown in FIG. 3 represents a PBP range whose central value is equal to a BP value which is predicted to be most probably measured by the BP measuring means 70 at an arbitrary time in the interval between the last and next BP measuring operations and within which a BP value of the patient, which will be measured by the BP measuring means 70 at the arbitrary time, is predicted to fall with the probability of 90%. The PBP range whose central value is equal to the central value PBP0 is represented by the future-side end of the triangular area 104 indicated by the vertical line 106. In view of the triangular area 104, the medical person who attends to the patient can see the range and probability of change of BP of the patient and accordingly can make an accurate decision on whether or not he or she should quickly give any treatments to the patient.

Moreover, in the BP monitoring apparatus 8, the period changing means 114 changes the predetermined period $T_{BP}$ to the shorter period $T_{BP'}$ when the upper and/or lower limit value $PBP_{max}$, $PBP_{min}$ of the PBP range determined by the range determining means 100 does not fall within the upper or lower limit value $BP_U$, $BP_L$ of the predetermined normal BP range, that is, when it can be predicted that the BP of the patient will go out of the normal BP range in future. Therefore, the present monitoring apparatus 8 can more quickly find an abnormal BP value of the patient and generate an alarm sound to inform the medical person of the occurrence of abnormality to the patient.

The present BP monitoring apparatus 8 includes the measured-BP displaying means 74 which displays the trend graph (i.e., the diagonal line 76) of the BP values measured by the BP measuring means 70, in the two-dimensional coordinate system defined by the time axis 78 indicative of the times when the BP values are measured by the BP measuring means 70 and the BP axis 80 indicative of the BP values measured by the BP measuring means 70; the central-value displaying means 92 which displays, on the two-dimensional coordinate system, the graphical representation (i.e. the broken line 94) of the central value PBP0 determined by the central-value determining means 88; and the range displaying means 102 which displays, on the two-dimensional coordinate system, the graphical representation (i.e. the triangular area 104) of the PBP range determined by the range determining means 100. Since the central value PBP0 and the PBP range are displayed on the two-dimensional coordinate system on which the trend graph of the measured BP values is displayed, the medical person and even the patient can easily and objectively grasp the range and probability of change of BP of the patient.

Moreover, the BP monitoring apparatus 8 includes the EBP determining means 86 which iteratively determines an estimated BP ("EBP") value of the patient based on the pulse-wave propagation time $DT_{RP}$ determined for each pulse of the patient, according to the predetermined $DT_{RP}$-EBP relationship (i.e., the expression (2)); and the central-value modifying means 90 which modifies the central value PBP0 determined by the central-value determining means 88, based on one or more EBP values determined by the EBP determining means 86. In view of the modified central value PBP0', the medical person can more accurately predict the future change of BP of the patient.

In the BP monitoring apparatus 8, the BP measuring means or device 70 includes the inflatable cuff 10 and measures a BP value of the patient by changing the pressing pressure (i.e., air pressure) of the cuff 10 applied to the body portion (e.g., upper arm 12) of the patient. That is, the BP measuring means 70 non-invasively performs each BP measurement, which leads to relieving the patient of the burden of being physically invaded for each BP measurement using, e.g., a catheter.

The BP monitoring apparatus 8 includes the period re-changing means 116 which re-changes the short period $T_{BP'}$ back to the initial, long period $T_{BP}$ when the upper and lower limit values $PBP_{max}$, $PBP_{min}$ of the modified PBP range determined by the range determining means 100 falls within the upper and lower limit values $BP_U$, $BP_L$ of the predetermined normal BP range after the initial long period $T_{BP}$ is changed to the short period $T_{BP'}$ by the period changing means 114. The fact that the modified PBP range now falls within the normal BP range after the initial long period $T_{BP}$ has been changed to the short period $T_{BP'}$ means that the BP of the patient that has been predicted to go out of the normal BP range is now predicted not to go out of the normal BP range. Accordingly, the period re-changing means 116 re-changes the short period $T_{BP'}$ back to the initial, long period $T_{BP}$. Thus, the BP measuring means 70 measures a BP value of the patient at the long period $T_{BP}$, which leads to relieving the patient of the burden of being measured at the short period $T_{BP'}$.

While the present invention has been described in its preferred embodiment, the present invention may be otherwise embodied.

For example, in the illustrated embodiment, the central-value determining means 88 applies the method of least squares to the BP values measured by the BP measuring means 70 and determines the straight line which approximates the measured BP values and represents the central value PBP0 of the patient. However, it is possible to determine a central value PBP0 of the patient in a different manner. For example, when each BP measuring operation is carried out, the rate of change of the BP value measured in the last or current BP measuring operation from that measured in the prior BP measuring operation is calculated, and an average of a plurality of change-rate values calculated in a plurality of BP measuring operations is calculated. Assuming that the thus calculated change-rate average indicates a future rate of change of the BP of the patient, a central value PBP0 of the patient at a future or later time can be predicated based on the change-rate average.

In the illustrated embodiment, the BP measuring means or device 70 employs the inflatable cuff 10 and non-invasively measures a BP value of a living subject. However, the BP measuring device 70 may employ a catheter which is adapted to be inserted into an arterial vessel of a living subject, and may measure a BP value of the subject through the catheter as well known in the art.

Figure 10:
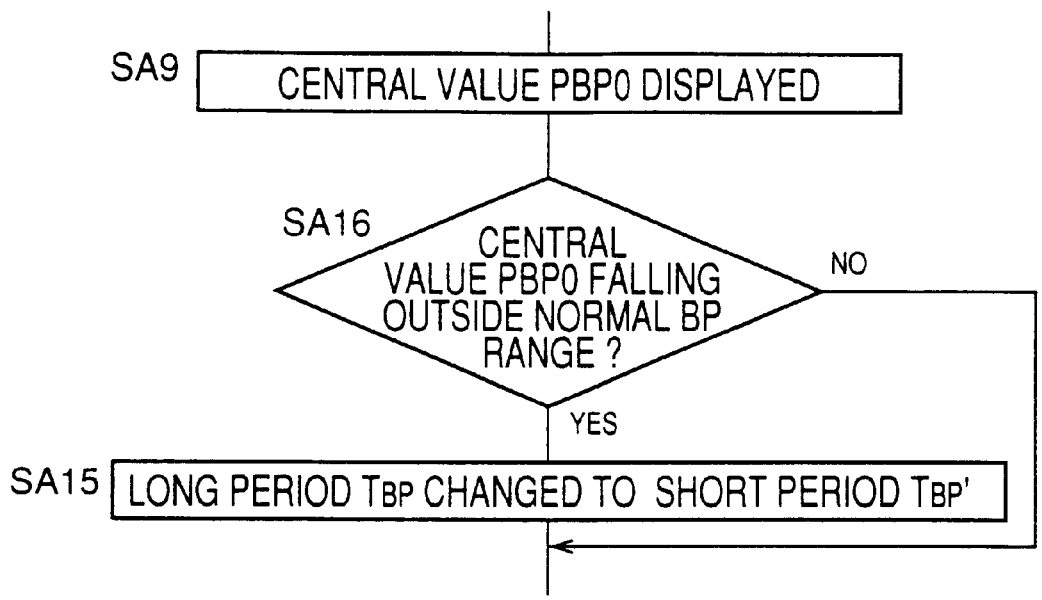
FIG. 10 is a flow chart representing a modified BP measuring routine according to which the control device of the apparatus of FIG. 1 is operated for measuring a BP value of the living subject.
Figure 11:
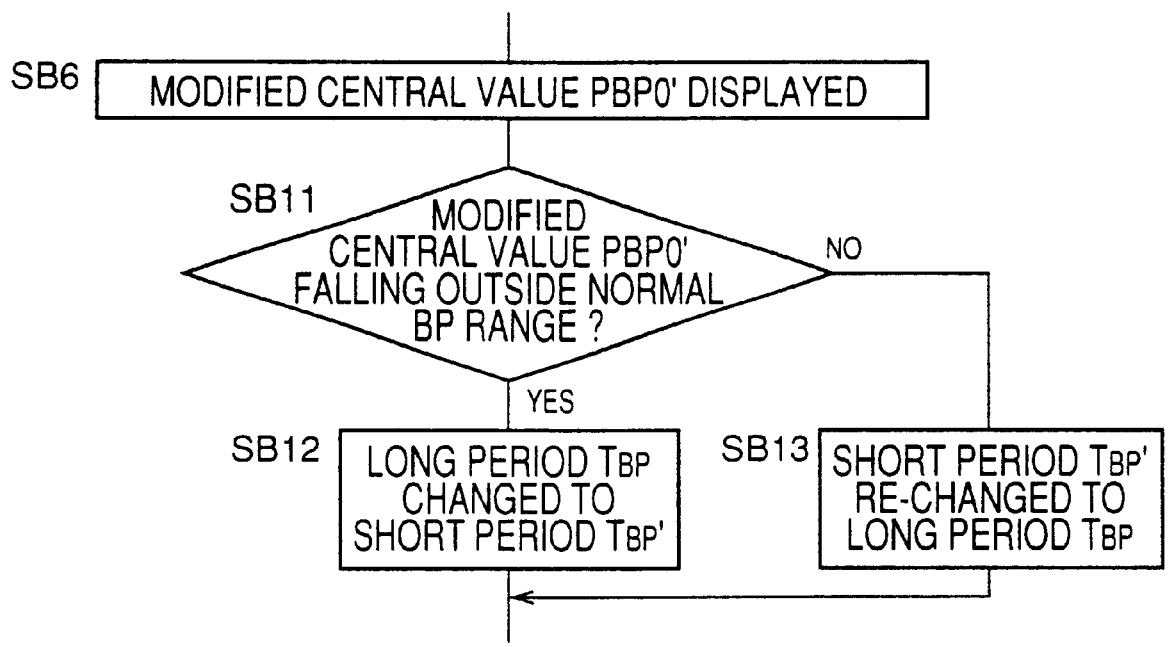
FIG. 11 is a flow chart representing a modified BP estimating routine according to which the control device of the apparatus of FIG. 1 is operated for estimating a BP value of the living subject.

In the illustrated embodiment, the range determining means 100 determines the PBP range whose central value is equal to the central value PBP0 and within which the BP value measured in the next BP measuring operation is predicted to fall with the predetermined probability, and the period changing means 114 changes the predetermined period $T_{BP}$ to the short period $T_{BP'}$ when the thus determined PBP range does not completely fall within the predetermined normal BP range. However, the range determining means 100 may be omitted. In this case, the period changing means 114 may change, based on the central value PBP0 or the modified central value PBP0', the predetermined period $T_{BP}$ to the short period $T_{BP'}$, according to a modified BP measuring routine shown in FIG. 10 and a modified EBP determining routine shown in FIG. 11. At Step SA16 of FIG. 10, the CPU 29 judges whether the central value PBP0 falls outside the predetermined normal BP range and, at Step SB15 of FIG. 11, the CPU 29 judges whether the modified central value PBP0' falls outside the predetermined normal BP range. After the initial long period $T_{BP}$ is thus changed to the short period $T_{BP'}$ at Step SA15 or SB12, the CPU 29 may judge at Step SB15 that a subsequent modified central value PBP0' falls within the normal BP range. In the latter case, the CPU 29 as the period re-changing means 116 re-changes, at Step SB13, the short period $T_{BP'}$ back to the initial long period $T_{BP}$.

In addition, the predetermined normal BP range employed at Step SA14 and SB11, or SA16 and SB15, may be replaced with a single reference BP value, such as the upper limit BP value $BP_U$ only, or the lower limit BP value $BP_L$ only, shown in FIG. 3 or FIG. 9.

In the illustrated embodiment, the range displaying means 102 displays the PBP range on the display device 32. However, the range displaying means 102 may be omitted. Even in this case, not only the trend graph of the BP values measured by the BP measuring means 70 but also the graph representing the central value PBP0 determined by the central-value determining means 88 are displayed on the two-dimensional coordinate system defined by the time axis 78 and the BP axis 80 by the measured-BP displaying means 74 and the central-value displaying means 92. From the graphs displayed on the display device 32, the medical person can easily and objectively recognize the future change of BP of the patient.

In the illustrated embodiment, the central value PBP0 is modified based on one or more EBP values by the central-value modifying means 90. Since, however, each EBP value corresponds to a pulse-wave propagation time $DT_{RP}$ or a pulse-wave propagation velocity $V_M$, as defined by the expression (2) or (3), the central value PBP0 may be modified with the parameter $DT_{RP}$ or $V_M$.

It is to be understood that the present invention may be embodied with other changes, improvements, and modifications that may occur to one having skill in the art without departing from the scope and spirit of the invention defined in the appended claims.

What is claimed is:

1. A blood-pressure monitoring apparatus comprising:
a measuring device which periodically measures a blood-pressure value of a living subject at a predetermined period; and
predicting means for predicting, based on a plurality of blood-pressure values measured by the measuring device, a blood-pressure value of the living subject at a time later as defined by a predetermined time interval than when a last one of the plurality of blood-pressure values is measured by the measuring device.

2. An apparatus according to claim 1, wherein the predicting means comprises central-value determining means for determining, as the predicted blood-pressure value, a central value of a blood-pressure range within which the blood pressure of the living subject is predicted, based on the plurality of blood-pressure values, to fall at the later time.

3. An apparatus according to claim 1, wherein the measuring device comprises an inflatable cuff, the measuring device periodically measuring a blood-pressure value of the living subject while changing a pressing pressure of the cuff applied to a body portion of the subject.

4. An apparatus according to claim 1, further comprising period changing means for changing, when the predicted blood-pressure value does not fall within a reference blood-pressure range, the predetermined period to a changed period shorter than the predetermined period, so that the measuring device measures a blood-pressure value of the living subject at the changed period.

5. An apparatus according to claim 1, further comprising period changing means for changing, when the predicted blood-pressure value is greater than a reference blood-pressure value, the predetermined period to a changed period shorter than the predetermined period, so that the measuring device measures a blood-pressure value of the living subject at the changed period.

6. An apparatus according to claim 1, further comprising period changing means for changing, when the predicted blood-pressure value is smaller than a reference blood-pressure value, the predetermined period to a changed period shorter than the predetermined period, so that the measuring device measures a blood-pressure value of the living subject at the changed period.

7. An apparatus according to claim 1, further comprising:
measured-blood-pressure-value displaying means for displaying a graph representing a time-wise trend of the plurality of blood-pressure values measured by the measuring device, on a two-dimensional coordinate system defined by a first axis indicative of a plurality of times at which the plurality of blood-pressure values are measured by the measuring device, respectively, and a second axis indicative of the plurality of blood-pressure values measured by the measuring device; and
predicted-blood-pressure-value displaying means for displaying, on the coordinate system, a graph representing the blood-pressure value predicted by the predicting means.

8. An apparatus according to claim 1, further comprising:
probability calculating means for calculating a probability with which a blood-pressure value of the living subject measured by the measuring device at the later time is equal to the predicted blood-pressure value, according to a predetermined relationship between time and probability;
probability-distribution calculating means for calculating, based on the calculated probability, a normal distribution of probability of the blood-pressure value of the living subject measured by the measuring device at the later time; and
range determining means for determining a blood-pressure range whose central value is equal to the predicted blood-pressure value and within which the blood-pressure value of the living subject measured by the measuring device at the later time falls with a predetermined probability.

9. An apparatus according to claim 8, further comprising period changing means for changing, when at least one of an upper limit value and a lower limit value of the determined blood-pressure range does not fall within a reference blood-pressure range, the predetermined period to a changed period shorter than the predetermined period, so that the measuring device measures a blood-pressure value of the living subject at the changed period.

10. An apparatus according to claim 8, further comprising period changing means for changing, when at least one of an upper limit value and a lower limit value of the determined blood-pressure range is greater than a reference blood-pressure value, the predetermined period to a changed period shorter than the predetermined period, so that the measuring device measures a blood-pressure value of the living subject at the changed period.

11. An apparatus according to claim 8, further comprising period changing means for changing, when at least one of an upper limit value and a lower limit value of the determined blood-pressure range is smaller than a reference blood-pressure value, the predetermined period to a changed period shorter than the predetermined period, so that the measuring device measures a blood-pressure value of the living subject at the changed period.

12. An apparatus according to claim 8, further comprising:
measured-blood-pressure-value displaying means for displaying a graph representing a time-wise trend of the plurality of blood-pressure values measured by the measuring device, on a two-dimensional coordinate system defined by a first axis indicative of a plurality of times at which the plurality of blood-pressure values are measured by the measuring device, respectively, and a second axis indicative of the plurality of blood-pressure values measured by the measuring device;
predicted-blood-pressure-value displaying means for displaying, on the coordinate system, a graph representing the blood-pressure value predicted by the predicting means; and
range displaying means for displaying, on the coordinate system, a graph representing the blood-pressure range determined by the range determining means.

13. An apparatus according to claim 1, further comprising:
pulse-wave-propagation-information obtaining means for iteratively obtaining, from the living subject, a set of information relating to propagation of a pulse wave through an arterial vessel of the subject;
estimating means for iteratively estimating a blood-pressure value of the living subject, based on each set of information of the iteratively obtained sets of information, according to a predetermined relationship between pulse-wave-propagation information and blood pressure; and
predicted-blood-pressure-value modifying means for modifying, based on the estimated blood-pressure value, the blood-pressure value predicted by the predicting means.

14. An apparatus according to claim 13, further comprising:
   period changing means for changing, when the predicted blood-pressure value does not fall within a reference blood-pressure range, the predetermined period to a changed period shorter than the predetermined period, so that the measuring device measures a blood-pressure value of the living subject at the changed period; and
   period re-changing means for re-changing, when the modified blood-pressure value falls within the reference blood-pressure range after the predetermined period is changed to the changed period, the changed period back to the predetermined period, so that the measuring device measures a blood-pressure value of the living subject at the predetermined period.

15. An apparatus according to claim 13, further comprising:
   period changing means for changing, when the predicted blood-pressure value is greater than a reference blood-pressure value, the predetermined period to a changed period shorter than the predetermined period, so that the measuring device measures a blood-pressure value of the living subject at the changed period; and
   period re-changing means for re-changing, when the modified blood-pressure value is not greater the reference blood-pressure value after the predetermined period is changed to the changed period, the changed period back to the predetermined period, so that the measuring device measures a blood-pressure value of the living subject at the predetermined period.

16. An apparatus according to claim 13, further comprising:
   period changing means for changing, when the predicted blood-pressure value is smaller than a reference blood-pressure value, the predetermined period to a changed period shorter than the predetermined period, so that the measuring device measures a blood-pressure value of the living subject at the changed period; and
   period re-changing means for re-changing, when the modified blood-pressure value is not smaller than the reference blood-pressure value after the predetermined period is changed to the changed period, the changed period back to the predetermined period, so that the measuring device measures a blood-pressure value of the living subject at the predetermined period.

17. An apparatus according to claim 13, further comprising:
   probability calculating means for calculating a probability with which a blood-pressure value of the living subject measured by the measuring device at the later time is equal to the predicted blood-pressure value, according to a predetermined relationship between time and probability;
   probability-distribution calculating means for calculating, based on the calculated probability, a normal distribution of probability of the blood-pressure value of the living subject measured by the measuring device at the later time; and
   range determining means for determining a blood-pressure range whose central value is equal to the predicted blood-pressure value and within which the blood-pressure value of the living subject measured by the measuring device at the later time falls with a predetermined probability.

18. An apparatus according to claim 17, wherein the probability calculating means comprises means for calculating a probability with which a blood-pressure value of the living subject measured by the measuring device at the later time is equal to the modified blood-pressure value, according to the predetermined relationship between time and probability, the probability-distribution calculating means comprises means for calculating, based on the calculated probability, a normal distribution of probability of the blood-pressure value of the living subject measured by the measuring device at the later time, and the range determining means comprises means for determining a modified blood-pressure range whose central value is equal to the modified blood-pressure value and within which the blood-pressure value of the living subject measured by the measuring device at the later time falls with the predetermined probability, and wherein the apparatus further comprises period changing means for changing, when at least one of an upper limit value and a lower limit value of the determined blood-pressure range does not fall within a reference blood-pressure range, the predetermined period to a changed period shorter than the predetermined period, so that the measuring device measures a blood-pressure value of the living subject at the changed period; and period re-changing means for re-changing, when at least one of an upper limit value and a lower limit value of the modified blood-pressure range falls within the reference blood-pressure range after the predetermined period is changed to the changed period, the changed period back to the predetermined period, so that the measuring device measures a blood-pressure value of the living subject at the predetermined period.

19. An apparatus according to claim 17, wherein the probability calculating means comprises means for calculating a probability with which a blood-pressure value of the living subject measured by the measuring device at the later time is equal to the modified blood-pressure value, according to the predetermined relationship between time and probability, the probability-distribution calculating means comprises means for calculating, based on the calculated probability, a normal distribution of probability of the blood-pressure value of the living subject measured by the measuring device at the later time, and the range determining means comprises means for determining a modified blood-pressure range whose central value is equal to the modified blood-pressure value and within which the blood-pressure value of the living subject measured by the measuring device at the later time falls with the predetermined probability, and wherein the apparatus further comprises period changing means for changing, when at least one of an upper limit value and a lower limit value of the determined blood-pressure range is greater than a reference blood-pressure value, the predetermined period to a changed period shorter than the predetermined period, so that the measuring device measures a blood-pressure value of the living subject at the changed period; and period re-changing means for re-changing, when at least one of an upper limit value and a lower limit value of the modified blood-pressure range is not greater than the reference blood-pressure value after the predetermined period is changed to the changed period, the changed period back to the predetermined period, so that the measuring device measures a blood-pressure value of the living subject at the predetermined period.

20. An apparatus according to claim 17, wherein the probability calculating means comprises means for calculating a probability with which a blood-pressure value of the living subject measured by the measuring device at the later time is equal to the modified blood-pressure value, according to the predetermined relationship between time and probability, the probability-distribution calculating means comprises means for calculating, based on the calculated probability, a normal distribution of probability of the blood-pressure value of the living subject measured by the measuring device at the later time, and the range determining means comprises means for determining a modified blood-pressure range whose central value is equal to the modified blood-pressure value and within which the blood-pressure value of the living subject measured by the measuring device at the later time falls with the predetermined probability, and wherein the apparatus further comprises period changing means for changing, when at least one of an upper limit value and a lower limit value of the determined blood-pressure range is smaller than a reference blood-pressure value, the predetermined period to a changed period shorter than the predetermined period, so that the measuring device measures a blood-pressure value of the living subject at the changed period; and period re-changing means for re-changing, when at least one of an upper limit value and a lower limit value of the modified blood-pressure range is not smaller than the reference blood-pressure value after the predetermined period is changed to the changed period, the changed period back to the predetermined period, so that the measuring device measures a blood-pressure value of the living subject at the predetermined period.

* * * * *